US012600767B2

(12) United States Patent
Beidler et al.

(10) Patent No.: US 12,600,767 B2
(45) Date of Patent: *Apr. 14, 2026

(54) COMPOUNDS AND METHODS TARGETING EPIREGULIN

(71) Applicant: Eli Lilly and Company, Indianapolis, IN (US)

(72) Inventors: Catherine Brautigam Beidler, Poway, CA (US); Jeffrey Streetman Boyles, Indianapolis, IN (US); Daniel Scott Girard, San Diego, CA (US); Shannon Marie Harlan, Carmel, IN (US); Michael Parvin Johnson, Carmel, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/748,405

(22) Filed: May 19, 2022

(65) Prior Publication Data

US 2022/0372124 A1 Nov. 24, 2022

Related U.S. Application Data

(60) Provisional application No. 63/191,496, filed on May 21, 2021.

(51) Int. Cl.
| | |
|---|---|
| *C07K 16/22* | (2006.01) |
| *A61P 25/04* | (2006.01) |
| *G01N 33/74* | (2006.01) |

(52) U.S. Cl.
CPC .............. *C07K 16/22* (2013.01); *A61P 25/04* (2018.01); *G01N 33/74* (2013.01); *C07K 2317/76* (2013.01); *C07K 2317/77* (2013.01); *C07K 2317/92* (2013.01); *G01N 2333/485* (2013.01)

(58) Field of Classification Search
None
See application file for complete search history.

(56) References Cited

U.S. PATENT DOCUMENTS

| | | | |
|---|---|---|---|
| 7,435,590 | B2 | 10/2008 | Komurasaki |
| 8,613,921 | B2 | 12/2013 | Beidler et al. |
| 9,556,264 | B2 | 1/2017 | Shiraiwa et al. |
| 10,005,832 | B2 | 6/2018 | Yoshida et al. |
| 10,852,304 | B2 | 12/2020 | Couto et al. |
| 2004/0202707 | A1 | 10/2004 | Muller |
| 2006/0034840 | A1* | 2/2006 | Agus ........................ A61P 29/00 424/143.1 |
| 2015/0320861 | A1* | 11/2015 | Kersten .............. C07K 16/2863 514/266.4 |
| 2016/0159919 | A1 | 6/2016 | Suzuki et al. |
| 2018/0196057 | A1 | 7/2018 | Couto et al. |

FOREIGN PATENT DOCUMENTS

| | | |
|---|---|---|
| WO | 2004/009776 A2 | 1/2004 |
| WO | 2012/138510 A1 | 10/2012 |
| WO | 2018034301 A1 | 2/2018 |
| WO | 2021/262662 A1 | 12/2021 |

OTHER PUBLICATIONS

Roepstorff et al., Traffic, 10:1115-1127, 2009.*
International Search Report for PCT/US2022/030058, Sep. 12, 2022, Eli Lilly and Company, Inc.
IPRP, International Written Opinion for PCT/US2022/030058, Sep. 12, 2022, Eli Lilly and Company, Inc.
Beidler, et al, "Generation and Activity of a Humanized Monoclonal Antibody That Selectively Neutralizes the Epidermal Growth Factor Receptor Ligands Transforming Growth Factor-a and Epiregulin" J. Pharmacology and Experimental Therapeutics, May 2014, 349(2):330-343.
Boyles, et al, "Structural basis of selectivity and neutralizing activity of a TGFa/epiregulin specific antibody", The Protein Society, 2016, vol. 25:2026-2036.
Iijima Mariko et al, "Epiregulin-blocking antibody inhibits epiregulin-dependent EGFR signaling", Biochemical and Biophysical Research Communications, Elsevier, Amsterdam NL, vol. 489, No. 1, Mar. 6, 2017 (Mar. 6, 2017) , pp. 83-88. XP085059730.
Kado Yuji et al: "Epiregulin Recognition Mechanisms by Anti-epiregulin Antibody 9E5", Journal of Biological Chemistry, vol. 291, No. 5, Jan. 1, 2016 (Jan. 1, 2016), pp. 2319-2330.
Lee Young-Hun et al: "Construction and characterization of functional anti-epiregulin humanized monoclonal 1-13 antibodies", Biochemical and Biophysical Research Communications, Elsevier, Amsterdam NL, vol. 441, No. 4, Nov. 12, 2013 (Nov. 12, 2013), pp. 1011-1017. XP028787982.
Martin Loren J. et al: "Epiregulin and EGFR interactions are involved in pain processing", The Journal of Clinical Investigation, vol. 127, No. 9, Sep. 1, 2017 (Sep. 1, 2017), pp. 3353-3366.
Sloan-Lancaster, et al, Evaluation of the Safety, Pharmacokinetics, Pharmacodynamics, and Efficacy After Single and Multiple Dosings of LY3016859 in Healthy Subjects and Patients With Diabetic Nephropathy:Clinical Pharmacology in Drug Development 2018, 7(7) 759-772.
International Preliminary Report on Patentability/Written Opinion of the International Searching Authority for PCT/US2021/038394, 8 pages, Dec. 13, 2022.
International Search Report issued by the European Patent Office for PCT/US2021/038394, 8 pages, Oct. 15, 2021.

(Continued)

*Primary Examiner* — Marianne P Allen
(74) *Attorney, Agent, or Firm* — Neelaabh Shankar

(57) ABSTRACT

The present invention relates to epiregulin antibodies, compositions comprising the same, and methods of making and/or using the antibodies and/or compositions thereof for chronic pain disorders such as chronic osteoarthritis pain, or chronic diabetic peripheral neuropathy pain, or chronic low back pain.

4 Claims, 6 Drawing Sheets

Specification includes a Sequence Listing.

(56) References Cited

OTHER PUBLICATIONS

Anonymous: "Chronic Pain Master Protocol (CPMP): A Study of LY3016859 in Participants with Osteoarthritis", ClinicalTrails.gov Identifier: NCT04456686, 2021.

Kersten et al., "Epidermal growth factor receptor-inhibition (EGFR-I) in the treatment of neuropathic pain", British Journal of Anaesthesia 2015; 115(5):761-767.

Leung, et al., "TNF-α and neuropathic pain—a review" Journal of Neuroinflammation, 7:27, 2010; 11 pages.

Schneider et al., "The Epidermal Growth Factor Receptor Ligands at a Glance". J Cell Physiol. 2009; 218(3):460-466.

Whitten, et al., "Treating Chronic Pain: New Knowledge, More Choices", The Permanente Journal, 9(4): 9-18, Fall 2005.

Roepstorff et al., "Differential Effects of EGFR Ligands on Endocytic Sorting of the Receptor" Traffic, 10:1115-1127, 2009.

* cited by examiner

A

B

EREG Mutant ELISA

FIGURE 5

COMPOUNDS AND METHODS TARGETING EPIREGULIN

REFERENCE TO SEQUENCE LISTING SUBMITTED ELECTRONICALLY

The present application includes a Sequence Listing in ASCII format. The Sequence Listing is provided as a file entitled X30020 sequence listing ST.25 created May 18, 2022, which is 19927 bytes in size. The information in the electronic format of the sequence listing is incorporated herein by reference in its entirety.

The present invention relates to compounds, pharmaceutical compositions, and methods, which include antibodies directed against human Epiregulin, and their use in the treatment of chronic pain, including nociceptive, neuropathic, and mixed pain, and in particular, the treatment of osteoarthritis (OA) pain, or diabetic peripheral neuropathy pain (DPNP), or chronic low back pain (CLBP).

Chronic pain is divided into different categories based on the mechanism: nociceptive, neuropathic, and mixed. Nociceptive pain is caused by stimuli that potentially or actually cause an injury to non-neuronal tissues. This activates nociceptive receptors in the peripheral sensory system. Pain due to osteoarthritis is a classic example of somatic nociceptive pain. Neuropathic pain is caused by injuries to or disease of the central or peripheral nervous system, leading to maladaptive hypersensitivity of the sensory nervous system. Pain due to diabetic peripheral neuropathy is a classic example of peripheral neuropathic pain. Conditions that exhibit features of both nociceptive and neuropathic pain, such as chronic low back pain, are categorized as mixed pain.

Chronic pain is a highly prevalent condition with huge societal impact. In 2016, an estimated 20.4% of the adult population in the United States experienced chronic pain, defined as pain on most days, or every day in the past 6 months, based on data from the National Health Interview Survey. An estimated 8% of the population had chronic pain that limited their lives or work activities on most days or every day in the past 6 months. As a result, chronic pain is a leading cause for health care expenditure with the annual cost for managing chronic pain in the United States in 2010 estimated at approximately $635 billion. Despite the high disease burden and societal impact, management of chronic pain is currently unsatisfactory. Nonpharmacologic therapy alone is seldom adequate for pain relief or functional improvement, and available pharmacologic therapies vary and offer modest benefit and some have significant safety risks. Presently, the most frequently used drugs to alleviate the most common types of chronic pain are acetaminophen, nonsteroidal anti-inflammatory drugs, and opioids. Gabapentinoids, other anticonvulsants (such as sodium divalproate, carbamazepine, or lamotrigine) and some antidepressants (such as tricyclics or duloxetine) can be used for some specific pain disorders. The current pharmacologic armamentarium typically provides low levels of efficacy, and have tolerability issues, and/or deleterious side effects. Opioids are effective against acute pain, but they are a limited treatment option for chronic pain because of high abuse risk and potentially serious adverse reactions. The physical, emotional, and financial impact of chronic pain on the patient and society, combined with a lack of efficacious and tolerable treatment options, make it a significant unmet medical need.

Epiregulin is a member of the epidermal growth factor receptor (EGFR) family of ligands which compromise 7 ligands: TGF-α (TGFA), Epiregulin (EREG), EGF, Heparin-Binding EGF (HB-EGF), Epigen (EPGN), Amphiregulin (AREG) and Betacellulin (BTC) (Schneider M R, Wolf E. The epidermal growth factor receptor ligands at a glance. *J Cell Physiol.* 2009; 218 (3): 460-466). In addition to EGFR (ErbB1) there are 3 additional receptors within this family of receptors (ErbB2, ErbB3 and ErbB4), of which ErbB3 and ErbB4 can bind the neuregulin family of ligands as well as select members of the EGFR family of ligand (epiregulin, betacellulin and HB-EGF). These ligands are synthesized as transmembrane proteins that are proteolytically cleaved to produce soluble ligands that can act in paracrine or autocrine manner to regulate various biological processes. Epiregulin can bind to both EGFR and ErbB4 to induce signaling through homodimerization or ligand induced heterodimerization with ErbB2 or ErbB3.

Epiregulin signaling contributes to a wide range of physiological conditions such as inflammation, wound healing and angiogenesis (Riese et al. Epiregulin: Roles in Normal Physiology and Cancer, Semin Cell Dev Biol. 2014, 0:49-56). Epiregulin signaling through the EGFR receptor homo or heterodimer pairs allows potential activation of numerous downstream signaling pathways such as ERK, MAPK, AP1, PI3K, JAK/STAT and NFKB. Activation of pathways such as JAK/STAT and NFKB are well documented in driving inflammation, whereas activation of AP1 signaling drives c-FOS and c-JUN activation which are markers of neural activation. Recently published data in preclinical models implicate a role for epiregulin in modulating chronic pain which is characterized by neuronal inflammation and neuronal activation suggesting a role for epiregulin signaling pathways modulating inflammatory and neuronal activation as potential mechanisms in chronic pain disorders. Reports indicate the EGFR pathway is involved in the pathogenesis of neuropathic pain (Kersten et al., Epidermal growth factor receptor-inhibition (EGFR-I) in the treatment of neuropathic pain. Br J Anaesth. 2015; 115 (5): 761-767). However, targeting the receptor with EGFR antibodies or EGFR tyrosine kinase inhibitors has been found to be associated with high incidence of gastrointestinal (GI) and skin adverse reactions which limit their potential use in chronic pain disorders.

Antibodies which bind to both TGFα and epiregulin are disclosed in WO 2012/138510, along with methods of treatment of diabetic nephropathy. LY3016859 is a monoclonal antibody that binds epiregulin and transforming growth factor α (TGF-α), which was tested in phase 1 clinical studies, and evaluated for safety, pharmacokinetics, pharmacodynamics, and efficacy in healthy subjects and patients with diabetic nephropathy (See Sloan-Lancaster, et al., Evaluation of the Safety, Pharmacokinetics, Pharmacodynamics, and Efficacy After Single and Multiple Dosings of LY3016859 in Healthy Subjects and Patients With Diabetic Nephropathy, Clinical Pharmacology in Drug Development 2018, 7 (7) 759-772). Sloan-Lancaster et al. recites that LY3016859 has greater affinity for TGFα than epiregulin, and further that LY3016859 administration did not result in any obvious effects on nephropathy disease-related biomarkers (See also Beidler, et al., J. Pharmacology and Experimental Therapeutics, 2014, 349 (2): 330-343). Nonlinear kinetics were seen suggesting target mediated drug disposition, and high doses were required for high levels of soluble target engagement. Notably there was a high frequency of anti-LY3016859 antibodies observed in both reported studies, but no clear impact on the pharmacokinetics, or target engagement, as indicated by dose and time dependent increases in circulating epiregulin measured in a drug tolerated assay. For treatment of chronic pain indications, antibodies that are more selective for epiregulin, have higher affinity, and are less likely to induce anti-drug antibody responses, represent an important unmet therapeutic need. There remains an unmet need for alternative and/or improved treatments for chronic pain disorders, including nociceptive, neuropathic, and mixed pain, and in particular in the treatment of osteoarthritis, or diabetic peripheral neuropathy, or chronic low back pain, and/or treatments for therapy resistant pain.

SUMMARY OF INVENTION

Embodiments of the present disclosure provide novel anti-human epiregulin antibodies, pharmaceutical compositions thereof, and methods of using these antibodies and compositions in the treatment of pain and chronic pain disorders. According to some embodiments, the present invention provides antibodies which comprise a light chain variable region (LCVR) and a heavy chain variable region (HCVR), wherein the LCVR comprises complementarity determining regions (CDRs) LCDR1, LCDR2 and LCDR3 and the HCVR comprises CDRs HCDR1, HCDR2 and HCDR3, and are selected from the groupings of CDR combinations provided in Table 1. Sequence identifiers used herein are listed in Table 1, and the sequences are provided in the amino acid and nucleotide sequence listing provided herein. Antibody 1 is a high-affinity fully human immunoglobulin G4 (IgG4) monoclonal antibody that binds to residues in the C-terminal regions of human epiregulin and prevents binding of human epiregulin to EGFR and activation of EGFR. Antibody 1 represents an improved anti-epiregulin antibody for human therapy, which possesses a combination of advantageous properties including enhanced affinity, selectivity, decreased risk of off-target and undesirable activities, decreased risk for immunogenicity, high potency and long duration of action, as well as other desirable properties, and provides improved means to block epiregulin and treat pain and chronic pain disorders.

TABLE 1

| Amino Acid and Nucleotide Sequences for Antibody 1 | |
| --- | --- |
| | Antibody 1 |
| SEQ ID HC | 1 |
| SEQ ID LC | 2 |
| SEQID HCVR | 3 |
| SEQID LCVR | 4 |
| SEQID HCDR1 | 5 |
| SEQID HCDR2 | 6 |
| SEQID HCDR3 | 7 |
| SEQID LCDR1 | 8 |
| SEQID LCDR2 | 9 |
| SEQID LCDR3 | 10 |
| SEQ ID: DNA HC | 11 |
| SEQ ID DNA LC | 12 |

Accordingly, embodiments of the present disclosure also provide antibodies comprising a LCVR and a HCVR wherein the LCVR has the amino acid sequence of SEQ ID NO: 4 and the HCVR has the amino acid sequence of SEQ ID NO: 3.

According to other embodiments, the present disclosure also provides antibodies comprising a LCVR and a HCVR wherein the LCVR has the amino acid sequence of SEQ ID NO: 4 and the HCVR has the amino acid sequence of SEQ ID NO: 3, with a hinge region and Fc region selected from SEQ ID NO: 40 and SEQ ID NO: 41.

In some embodiments, the present disclosure also provides antibodies comprising a LC having the amino acid sequence of SEQ ID NO: 2 and a HC having the amino acid sequence of SEQ ID NO: 1. According to other embodiments, the present disclosure also provides antibodies comprising a LC and a HC having amino acid sequences with at least 95% homology to the amino acid sequences of the LC having the amino acid sequence of SEQ ID NO: 2 and the HC having the amino acid sequence of SEQ ID NO: 1.

As used herein "Antibody 1" refers to an antibody having the HCDR1 amino acid sequence of SEQ ID NO: 5, the HCDR2 amino acid sequence of SEQ ID NO: 6, the HCDR3 amino acid sequence of SEQ ID NO: 7, the LCDR1 amino acid sequence of SEQ ID NO: 8, the LCDR2 amino acid sequence of SEQ ID NO: 9, the LCDR3 amino acid sequence of SEQ ID NO: 10, the HCVR amino acid sequence of SEQ ID NO: 3, the LCVR amino acid sequence of SEQ ID NO: 4, the HC amino acid sequence of SEQ ID NO: 1, the LC amino acid sequence of SEQ ID NO: 2, or encoded by the HC DNA sequence of SEQ ID NO: 11, or encoded by the LC DNA sequence of SEQ ID NO: 12. The framework and CDR sequences in each of the antibodies for which sequences are set forth herein are annotated using annotation rules in agreement with the method of North, et al., *J. Mol. Biol.* 2011:406: 228-256 unless otherwise specified.

The carboxy-terminal portion of each HC defines a constant region primarily responsible for effector functions, and in some embodiments of the present invention the antibodies have one or more modifications in the constant region of each HC that reduce effector functions. Preferably, embodiments of the present invention are IgG4 antibodies, and thus contain an IgG4 Fc region, or an Fc region derived from human IgG4, e.g., a modified IgG4 Fc region.

According to some embodiments, modifications in the constant region of both HCs which reduce effector functions, and amino acid substitutions are introduced into the IgG4 hinge and Fc regions. Thus, some embodiments have modifications in the constant region of both HCs which include the amino acid alanine at both residues 229 and 230 (EU Index positions 234-235) (exemplified in HC of Antibody 1, and illustrated in SEQ ID NO: 41), and further modifications in the constant region of both HCs promoting stability, including the amino acid proline at residue 223 (EU Index positions 228) (exemplified in HC of Antibody 1, and illustrated in SEQ ID NO: 40), and the deletion of the amino acid lysine at residue 442 (EU Index positions 447) (exemplified HC of SEQ ID NO: 1).

The antibodies of the present invention are believed to have a combination of particularly advantageous properties over prior art anti-epiregulin antibodies, including but not limited to, one or more of the following properties: 1) high binding affinity and desirable association and dissociation rates, 2) potency in neutralization of human epiregulin to achieve a pain mitigating response and in vivo efficacy, 3) sufficiently potent as a monotherapy for the treatment and/or prevention of pain disorders; 4) a sustained duration of action; 5) sufficiently limited injection site reactions, 6) acceptably low immunogenicity (i.e., sufficiently non-immunogenic in humans); 7) reduction of untoward skin rash reactions, and/or 8) desirable in vivo stability, physical and chemical stability including, but not limited to, thermal stability, solubility, low self-association, and pharmacokinetic characteristics which are acceptable for development and/or use in the treatment of pain disorders, for example chronic pain, including nociceptive, neuropathic, and mixed pain, and in particular in the treatment of chronic osteoarthritis pain, or chronic diabetic peripheral neuropathy pain, or chronic low back pain.

Embodiments of the present invention provide a significant advance over the prior art by providing antibodies against human epiregulin, compositions thereof and methods useful in the treatment, downregulation, or amelioration of pain disorders, through epiregulin neutralization, using a pharmacologically advantageous anti-human epiregulin antibody as provided in the embodiments described herein. Anti-human epiregulin antibodies of the present invention are capable of mitigating pain symptoms, improving pain pathophysiology, preferably, through inhibition of the pain response, particularly in chronic pain disorders and pain states. The use of such antibodies clinically may lead to extended relief of the pain associated disorder(s) being treated.

Further, there is a need for diagnostic anti-human epiregulin antibodies that are specific for human epiregulin, and possess improved binding affinity, and demonstrate enhanced sensitivity in human epiregulin determinations, and improved enzyme-linked immunosorbent assay (ELISA) assay conditions that result in minimal interference and broad dilutional linearity. According to some aspects of the present disclosure, anti-human epiregulin antibodies, including human epiregulin neutralizing antibodies, are provided which bind human epiregulin given by SEQ ID NO: 13. "Epiregulin" or "human epiregulin" refers to human epiregulin protein. As used herein epiregulin refers to the mature epiregulin peptide. Epiregulin (also known as EREG, EPR) is a 46-amino acid protein that belongs to the Epidermal Growth Factor (EGF) family of peptide hormones. Epiregulin is produced as a 162-amino acid transmembrane epiregulin precursor which is cleaved to release the 46-amino acid mature peptide of the following sequence: "VSITKCSSDMNGYCLHGQCIYLVDMSQNYCRCE-VGYTGVRCEHFFL" (SEQ ID NO: 13) (see for example Toyoda, et al., Molecular cloning of mouse epiregulin, a novel epidermal growth factor-related protein, expressed in the early stage of development. FEBS Lett. 1995; 377:403-7). Human epiregulin (SEQ ID NO: 14), as described and prepared in Example 2, may for example be used in in vitro experiments described herein. References to the ability of the antibodies as described herein to bind and/or to neutralize human epiregulin pertain also to their ability to bind and to neutralize human epiregulin in in vitro experiments.

As used herein, "human anti-epiregulin antibody" or "anti-human epiregulin antibody" refers to an antibody that binds to human epiregulin, and when administered in vitro or in vivo, results in an epiregulin activity-neutralizing and/or blocking response, such as at least one significantly lessened activity. For example, a desired reduction in epiregulin signaling as evidenced by a change in an epiregulin responsive molecular or cellular endpoint(s). As used herein, the terms "signaling" and "signal transduction" and "epiregulin-mediated" as they relate to epiregulin, refer to cellular and/or intercellular responses which result from the activity of epiregulin.

The term "antibody," as used herein, refers to an immunoglobulin molecule that binds an antigen. Embodiments of an antibody include a monoclonal antibody, polyclonal antibody, human antibody, humanized antibody, chimeric antibody, or conjugated antibody. The antibodies can be of any class (e.g., IgG, IgE, IgM, IgD, IgA) and any subclass (e.g., IgG1, IgG2, IgG3, IgG4). An exemplary antibody is an immunoglobulin G (IgG) type antibody comprised of four polypeptide chains: two heavy chains (HC) and two light chains (LC) that are cross-linked via inter-chain disulfide bonds. LCs are classified as kappa or lambda, which are each characterized by a specific constant region. Embodiments of the present invention may comprise an IgG1 or IgG4 antibody, and further comprise kappa light chains or lambda light chains. Preferably antibodies of the present invention comprise light chain constant regions which are kappa constant regions.

HCs are classified as gamma, mu, alpha, delta, or epsilon, and define the isotype of an antibody as IgG, IgM, IgA, IgD, or IgE, respectively. The amino-terminal portion of each of the four polypeptide chains includes a variable region of about 100-125 or more amino acids primarily responsible for antigen recognition. The carboxyl-terminal portion of each of the four polypeptide chains contains a constant region primarily responsible for effector functions. Each heavy chain is comprised of a heavy chain variable region (VH) and a heavy chain constant region. The constant region of the heavy chains contains CH1, CH2, and CH3 domains. CHI comes after the HCVR; the CH1 and HCVR form the heavy chain portion of an antigen-binding (Fab) fragment, which is the part of an antibody that binds antigen(s). CH2 comes after the hinge region and before CH3. CH3 comes after CH2 and is at the carboxy-terminal end of the heavy chain. The constant region of the light chains contains one domain, CL. CL comes after the LCVR; the CL and LCVR form the light chain portion of a Fab.

The antibodies of the present invention include IgG HCs which can be further divided into subclasses, e.g., IgG1, IgG2, IgG3, IgG4, and embodiments of the present disclosure may include one or more modifications in the constant region of each HC, for example that enhance or reduce effector function. The term "Fc region" as used herein refers to a region of an antibody, which comprises the CH2 and CH3 domains of the antibody heavy chain. Optionally, the Fc region may include a portion of the hinge region or the entire hinge region of the antibody heavy chain. IgG1 is known to induce antibody-dependent cell cytotoxicity (ADCC) and complement-dependent cytotoxicity (CDC), and Fc mutations described herein may reduce aggregation, reduce, or enhance ADCC or CDC activities (or other functions), and/or modify the pharmacokinetics of the antibodies. Embodiments of anti-human EREG antibodies described herein have reduced binding to the FcγR and C1q receptors, thereby reducing or eliminating the cytotoxicity which may be induced by antibodies with wild type IgG Fc regions. Thus, according to some embodiments, mutations are introduced in the Fc region at positions as described herein. Patient safety can be improved with sufficiently reduced or eliminated effector functions of such anti-human EREG antibodies comprising a modified Fc region, and in combination with other properties described herein, provide therapeutic agents with an improved profile of useful activities while avoiding undesirable activities.

When expressed in certain biological systems, antibodies are glycosylated in the Fc region. Typically, glycosylation occurs in the Fc region of the antibody at a highly conserved N-glycosylation site. N-glycans typically attach to asparagine. Antibodies may be glycosylated at other positions as well. Antibodies of the present disclosure are monoclonal antibodies. Monoclonal antibodies are antibodies derived from a single copy or clone including, for example, any eukaryotic, prokaryotic or phage clone, and not defined by the method by which it is produced. Monoclonal antibodies can be produced, for example, by hybridoma technologies, recombinant technologies, phage display technologies, synthetic technologies, e.g., CDR-grafting, or combinations of such or other technologies known in the art. The present disclosure contemplates the antibodies of the present invention are human or humanized antibodies. In the context of monoclonal antibodies, the terms "human" and "humanized" are well-known to those of ordinary skill in the art (Weiner LJ, J. Immunother. 2006; 29:1-9; Mallbris L, et al., J. Clin. Aesthet. Dermatol. 2016; 9:13-15). Exemplary embodiments of antibodies of the present disclosure also include antibody fragments or antigen-binding fragments, which comprise at least a portion of an antibody retaining the ability to specifically interact with an antigen such as Fab, Fab', F(ab')2, Fv fragments, scFv antibody fragments, disulfide-linked Fvs (sdFv), a Fd fragment and linear antibodies.

The amino terminal portion of each LC and HC includes a variable region of about 100-120 amino acids primarily al., "A New Clustering of Antibody CDR Loop Conformations", Journal of Molecular Biology, 406, 228-256 (2011)), or IMGT (the international ImMunoGeneTics database available on at www.imgt.org; see Lefranc et al., Nucleic Acids Res. 1999; 27:209-212).

For the purposes of the present disclosure, and except where specified otherwise, the North CDR definitions are used for the anti-epiregulin antibodies described herein, and assignment of amino acids to CDR domains within the LCVR and HCVR regions. Below Table 2 provides CDR sequences for Antibody 1, and/or Antibodies of the present disclosure, based on conventions of North, Kabat, Chothia, and/or IMGT respectively, generated using the SAbPred/ANARCI library (Dunbar and Deane, "ANARCI: antigen receptor numbering and receptor classification", Bioinformatics, 32, 298-300 (2016)).

TABLE 2

| Exemplary CDRs of Antibody 1 (or Antibodies of the present disclosure) | | | | | | |
| --- | --- | --- | --- | --- | --- | --- |
| Ab | HCDR1 | HCDR2 | HCDR3 | LCDR1 | LCDR2 | LCDR3 |
| North | TVSGGSI SSYYWS (SEQ ID NO: 5) | RIYPSGNT N (SEQ ID NO: 6) | ARGGLVM DV (SEQ ID NO: 7) | RASQSVEF SYLA (SEQ ID NO: 8) | YGASSRA T (SEQ ID NO: 9) | HQYGTN PFT (SEQ ID NO: 10) |
| Kabat | SYYWS (SEQ ID NO: 22) | RIYPSGNT NYNPSLKS (SEQ ID NO: 23) | GGLVMDV (SEQ ID NO: 24) | RASQSVEF SYLA (SEQ ID NO: 25) | GASSRAT (SEQ ID NO: 26) | HQYGTN PFT (SEQ ID NO: 27) |
| Chothia | GGSISSY (SEQ ID NO: 28) | YPSGN (SEQ ID NO: 29) | GGLVMDV (SEQ ID NO: 30) | RASQSVEF SYLA (SEQ ID NO: 31) | GASSRAT (SEQ ID NO: 32) | HQYGTN PFT (SEQ ID NO: 33) |
| IMGT | GGSISSY Y (SEQ ID NO: 34) | IYPSGNT (SEQ ID NO: 35) | ARGGLVM DV (SEQ ID NO: 36) | QSVEFSY (SEQ ID NO: 37) | GAS (SEQ ID NO: 38) | HQYGTN PFT (SEQ ID NO: 39) | responsible for antigen recognition via the CDRs contained therein. The VH and VL regions can be further subdivided into regions of hyper-variability, termed complementarity determining regions (CDRs), interspersed with regions that are more conserved, termed framework regions (FR). The CDRs are exposed on the surface of the protein and are important regions of the antibody for antigen binding specificity. Each VH and VL is composed of three CDRs and four FRs, arranged from amino-terminus to carboxyl-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues that form specific interactions with the antigen. The functional ability of an antibody to bind a specific antigen is largely influenced by the six CDRs. Assignment of amino acid residues to the CDRs may be done according to the well-known schemes, including those described in Kabat (Kabat et al., "Sequences of Proteins of Immunological Interest," National Institutes of Health, Bethesda, Md. (1991)), Chothia (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)), North (North et Antibody embodiments of the present disclosure possess a combination of several pharmacologically useful and important activities, and in one respect are capable of binding with high affinity to human epiregulin, and high specificity for human epiregulin, as well as other useful properties. The terms "bind" and "binds" as used herein are intended to mean, unless indicated otherwise, the ability of a protein or molecule to form attractive interactions with another protein or molecule, which result in proximity of the two proteins or molecules as determined by common methods known in the art. The phrase "specifically binds", as used herein in, refers to the affinity of an anti-epiregulin antibody for human epiregulin, and is intended to mean, unless indicated otherwise, a $K_D$ of less than about $2 \times 10^{-9}$ M, and preferably less than about $2 \times 10^{-11}$ M, and even more preferably, between about $2 \times 10^{-11}$ M and about $2 \times 10^{-12}$ M, as determined at about pH 7.4, by common methods known in the art, including use of MSD-SET (solution equilibrium titration) as described herein. The phrase "specifically binds" also indicates the relative affinity of an anti-epiregulin antibody for human epiregulin, as compared to other antigens, and in particular the EGFR-ligand TGFα, wherein the affinity for human epiregulin results in a specific recognition of human epiregulin and a lack of binding to other EGFR ligands tested.

Antibody embodiments of the present disclosure may be expressed and produced by a variety of techniques known in the art from constructs comprising sequences of the present embodiments. The terms "nucleic acid" or "polynucleotide" as used interchangeably herein, refer to polymers of nucleotides, including single-stranded and/or double-stranded nucleotide-containing molecules, such as DNA, cDNA and RNA molecules, incorporating native, modified, and/or analogs of, nucleotides. Polynucleotides of the present disclosure may also include substrates incorporated therein, for example, by DNA or RNA polymerase or a synthetic reaction. A DNA molecule of the present disclosure is a DNA molecule that comprises a non-naturally occurring polynucleotide sequence encoding a polypeptide having the amino acid sequence of at least one of the polypeptides in an antibody of the present invention (e.g., heavy chain, light chain, variable heavy chain, and variable light chain).

An isolated DNA encoding a HCVR or LCVR region can be converted to a full-length heavy chain gene by operably linking the respective HCVR or LCVR-encoding DNA to another DNA molecule encoding heavy or light chain constant regions to form a heavy or light chain respectively. The sequences of human, as well as other mammalian, heavy chain constant region genes are known in the art. DNA fragments encompassing these regions can be obtained, e.g., by standard PCR amplification.

The polynucleotides of the present disclosure can be expressed in a host cell after the sequences have been operably linked to an expression control sequence. The expression vectors are typically replicable in the host organisms either as episomes or as an integral part of the host chromosomal DNA. Commonly expression vectors will contain selection markers, e.g., tetracycline, neomycin, and dihydrofolate reductase, to permit detection of those cells transformed with the desired DNA sequences. The vectors containing the polynucleotide sequences of interest (e.g., the polynucleotides encoding the polypeptides of the antibody and expression control sequences) can be transferred into the host cell by well-known methods which vary depending on the type of cellular host.

The antibodies of the present disclosure can readily be produced in mammalian cells, of which non-limiting examples include CHO, NS0, HEK293 or COS cells. The host cells are cultured using techniques well known in the art. Mammalian expression of antibodies typically results in glycosylation. Glycosylation of antibodies is typically either N-linked or O-linked. N-linked glycosylation refers to the attachment of a carbohydrate moiety to the side chain of an asparagine residue. O-linked glycosylation refers to the attachment of a sugar, for example N-acetylgalactosamine, galactose, or xylose to a hydroxyamino acid. Typically, glycosylation occurs in the Fc region of the antibody at a highly conserved N-glycosylation site (e.g., position 297 in IgG1, according to IMGT or EU Index numbering). Glycosylation sites can be modified to alter glycosylation (e.g., blocking or reducing glycosylation or altering the amino acid sequence to produce additional or diverse glycosylation).

Mammalian expression of antibodies from IgG subclasses can result in clipping of C-terminal amino acids from one or both heavy chains; for example, one or two C-terminal amino acids can be removed for IgG1 antibodies. For IgG1 antibodies, if a C-terminal lysine is present, then it may be truncated or clipped off from the heavy chain during expression. Additionally, a penultimate glycine may also be truncated or clipped off from the heavy chain as well.

Mammalian expression of antibodies can also result in the modification of N-terminal amino acids. For example, where the N-terminal most amino acid of a heavy chain or light chain is a glutamine, it may be modified into pyro-glutamic acid.

An antibody of the present disclosure, or a pharmaceutical composition comprising the same, may be administered by parenteral routes, non-limiting examples of which are subcutaneous administration and intravenous administration. An antibody of the present disclosure may be administered to a patient with pharmaceutically acceptable carriers, diluents, or excipients in single or multiple doses. Pharmaceutical compositions of the present disclosure can be prepared by methods well known in the art (e.g., Remington: The Science and Practice of Pharmacy, 22nd ed. (2012), A. Loyd et al., Pharmaceutical Press) and comprise an antibody, as disclosed herein, and one or more pharmaceutically acceptable carriers, diluents, or excipients.

Uses of Antibody Embodiments of the Present Disclosure:

According to some embodiments, the anti-epiregulin antibodies of the present disclosure are useful in the treatment of pain disorders. As used herein, the term "pain disorder" or "pain disorders" refer to undesirable conditions that arise from excessive and/or chronic pain conditions in which epiregulin inhibition results in more homeostatic and less pathological pain states. Exemplary pain disorders contemplated to be treated by the antibodies of the disclosure described herein include chronic pain, including nociceptive, neuropathic, and mixed pain, and in particular, the treatment of osteoarthritis pain, or diabetic peripheral neuropathy pain, or low back pain, and chemotherapy induced peripheral neuropathy, particularly in chronic pain states.

According to other embodiments of the present invention, the anti-epiregulin antibodies are useful in diagnostic applications for epiregulin-mediated pain disorders. In some embodiments, the pain disorders are at least one of osteoarthritis (OA) pain, or diabetic peripheral neuropathy pain (DPNP), or chronic low back pain (CLBP). In some more specific embodiments, the pain disorder is osteoarthritis (OA).

The present disclosure further provides pharmaceutical compositions comprising an anti-epiregulin antibody of the present disclosure and one or more pharmaceutically acceptable carriers, diluents or excipients. Further, the present disclosure provides a method of treating a pain disorder, such as osteoarthritis pain, or diabetic peripheral neuropathy pain, or chronic low back pain, comprising administering to a patient in need thereof a pharmaceutical composition of the present disclosure.

In addition, the present disclosure provides a method of treating epiregulin-mediated diseases. More particularly, the present invention provides a method of treating a chronic pain disorder, such as osteoarthritis pain, or diabetic peripheral neuropathy pain, or chronic low back pain, comprising administering to a patient in need thereof an effective amount of an anti-epiregulin antibody of the present disclosure.

The present disclosure also provides an anti-epiregulin antibody of the present disclosure for use in therapy. More particularly, the present disclosure provides an anti-epiregulin antibody of the present disclosure for use in treatment of a chronic pain disorder, such as osteoarthritis pain, or diabetic peripheral neuropathy pain, or chronic low back pain.

In certain embodiments, the present disclosure provides the use of an anti-epiregulin antibody of the present disclosure, or a composition thereof, in the manufacture of a medicament for the treatment of one or more chronic pain disorders, such as osteoarthritis pain, or diabetic peripheral neuropathy pain, or chronic low back pain.

Antibodies of the present disclosure are useful in the identification of chronic pain disorders wherein epiregulin may contribute to the etiopathogenesis of the disorder. In further embodiments, the present disclosure provides a method of treating a chronic pain disorder in a patient. Such methods comprise the steps of contacting a patient sample with an anti-epiregulin antibody and detecting binding between human epiregulin in the patient sample and the antibody; and diagnosing the patient as having; at risk for; in need of treatment for; and/or at risk of symptoms relating to an epiregulin-mediated disorder when the presence of epiregulin in the patient sample is detected as above a reference value as observed in non-diseased individuals. According to some more specific embodiments of the methods of treating provided herein, such methods further include the steps of determining the reference value including the further steps of contacting a control standard with a first antibody which binds the same first epitope region of epiregulin as used in contacting the patient sample; contacting the control standard with a second antibody having a detectable label and which binds the same second epitope region of epiregulin as used in contacting the patient sample; and detecting a signal provided by the detectable signal. In some specific embodiments, the anti-epiregulin antibody comprises a combination of LC and HC CDRs provided in Table 1. In further embodiments, the second antibody comprises a combination of LCVR and HCVR provided in Table 1. In certain embodiments, the chronic pain disorder is one of osteoarthritis pain, or diabetic peripheral neuropathy pain, or chronic low back pain. In some embodiments, the patient sample is one of CSF, blood, serum, a tissue lysate, or plasma. According to some embodiments, the method further includes the steps of contacting the patient sample with a second anti-epiregulin antibody which binds a second epitope region of epiregulin, and has a detectable label, and detecting a signal provided by the detectable signal. In further embodiments, the second antibody comprises a combination of LC and HC CDRs provided in Table 1. In further embodiments, the second antibody comprises a combination of LCVR and HCVR provided in Table 1. According to certain embodiments, the first and second anti-epiregulin antibodies do not bin together.

According to some embodiments, the present disclosure provides a method of detecting epiregulin in a patient sample comprising the steps of contacting the patient sample with a first antibody which binds a first epitope region of epiregulin; contacting the patient sample with a second antibody which binds a second epitope region of epiregulin and has a detectable label; and detecting a signal provided by said detectable label. In some embodiments, the patient sample is one of blood, serum, a tissue lysate, or plasma. According to some more specific embodiments, the first epitope region of epiregulin partially overlaps with the second epitope region of epiregulin. Further, in some embodiments, said steps of contacting with the first and second antibodies occurs simultaneously. In some specific embodiments, the first antibody comprises a combination of LC and HC CDRs provided in Table 1. In further embodiments, the first antibody comprises a combination of LCVR and HCVR provided in Table 1.

According to some embodiments of the present disclosure, a method of quantifying epiregulin in a patient sample is provided. Such method includes the steps of contacting the patient sample with a first antibody which binds a first epitope region of epiregulin; contacting the patient sample with a second antibody which binds a second epitope region of epiregulin and said has a detectable label; and detecting the signal provided by said detectable label; contacting a control standard with a first antibody which binds the same first epitope region of epiregulin (as used in contacting the patient sample); contacting the control standard with a second antibody which binds the same second epitope region of epiregulin (as used in contacting the patient sample) and having a detectable label; and detecting a signal provided by said detectable signal. In some embodiments, the patient sample is one of blood, serum or plasma, or a tissue lysate. According to some more specific embodiments, the first epitope region of epiregulin partially overlaps with the second epitope region of epiregulin. Further, in some embodiments, said steps of contacting with the first and second antibodies occurs simultaneously. In some specific embodiments, the first antibody comprises a combination of LC and HC CDRs provided in Table 1. In further embodiments, the first antibody comprises a combination of LCVR and HCVR provided in Table 1. In some specific embodiments, the second antibody comprises a combination of LC and HC CDRs provided in Table 1. In further embodiments, the second antibody comprises a combination of LCVR and HCVR provided in Table 1.

According to some embodiments, a method of diagnosing an epiregulin-mediated disease or disorder is provided. Such method comprises the steps of contacting a patient sample with an anti-epiregulin antibody and detecting binding between epiregulin in the patient sample and the antibody. According to some specific embodiments, the method of diagnosing includes diagnosing the patient as having; at risk for; in need of treatment for; and/or at risk of symptoms relating to an epiregulin-mediated disorder when the presence of epiregulin in the patient sample is detected as above a reference value. According to some more specific embodiments, such methods further include the steps of determining the reference value including the steps of contacting a control standard with a first antibody which binds the same first epitope region of epiregulin as used in contacting the patient sample; contacting the control standard with a second antibody having a detectable label and which binds the same second epitope region of epiregulin as used in contacting the patient sample; and detecting a signal provided by the detectable signal. In some embodiments, the first antibody comprises a combination of LC and HC CDRs provided in Table 1. In further embodiments, the antibody comprises a combination of LCVR and HCVR provided in Table 1. Some embodiments of the method of diagnosing an epiregulin-mediated disease, provided herein, further includes the steps of contacting the patient sample with a second anti-epiregulin antibody which binds a second epitope region of epiregulin and has a detectable label; and detecting a signal provided by the detectable label. In some specific embodiments, the anti-epiregulin antibody comprises a combination of LC and HC CDRs provided in Table 1. In further embodiments, the antibody comprises a combination of LCVR and HCVR provided in Table 1. According to specific embodiments, the first epitope region of epiregulin partially overlaps with the second epitope region of epiregulin. According to certain embodiments, the first and second antibodies do not bin together. According to further embodiments, the reference value is established from healthy volunteer plasma, bodily fluids, or tissue lysates, and/or as determined by the skilled artisan for the appropriate reference group and sample source. In further embodiments, the pain disorder is one of osteoarthritis pain, or diabetic peripheral neuropathy pain, or chronic low back pain.

In an embodiment the present disclosure provides method of determining the human epiregulin level in a bodily fluid sample comprising: (a) contacting the bodily fluid sample with an anti-human epiregulin diagnostic monoclonal antibody, or antigen-binding fragment thereof, that specifically binds to human epiregulin comprising the amino acid sequence as in SEQ ID NO: 13, wherein the antibody, or antigen-binding fragment thereof, comprises: light chain complementarity determining regions LCDR1, LCDR2, and LCDR3 comprising the amino acid sequences SEQ ID NO: 8, SEQ ID NO: 9, and SEQ ID NO: 10, respectively, and heavy chain complementarity determining regions HCDR1, HCDR2, and HCDR3 comprising the amino acid sequences SEQ ID NO: 5, SEQ ID NO: 6, and SEQ ID NO: 7, respectively; (b) optionally, removing any non-specifically bound monoclonal antibody or, antigen-binding fragment thereof; and (c) detecting and/or quantifying the amount of monoclonal antibody, or antigen-binding fragment thereof, which is specifically bound to human epiregulin. Preferably, wherein said bodily fluid sample is a blood, serum or plasma sample, or cerebrospinal fluid sample, and said contacting occurs ex vivo.

In embodiments of the disclosure a patient is a human who has been diagnosed as having a medical risk, condition or disorder, such as one of the diseases or disorders described herein, in need of treatment with an antibody described herein. In those instances where the disorders which can be treated by the methods of the present invention are known by established and accepted classifications, such as osteoarthritis pain, or diabetic peripheral neuropathy pain, or chronic low back pain, their classifications can be found in various well-known medical texts. For example, the 5th edition of the Diagnostic and Statistical Manual of Mental Disorders (DSM-5) or similar texts provide a diagnostic tool for identifying certain disorders described herein (See also for example Scholz, et al., The IASP classification of chronic pain for ICD-11: chronic neuropathic pain. Pain. 2019 January; 160 (1): 53-59, and Treede et al., Chronic pain as a symptom or a disease: the IASP Classification of Chronic Pain for the International Classification of Diseases (ICD-11), PAIN: 2019 January 160:19-27)). Also, the International Classification of Diseases, Tenth Revision (ICD-10), provides classifications for certain disorders described herein. The skilled artisan will recognize that there are alternative nomenclatures, nosologies, and classification systems for diseases and disorders described herein, including those as described in the DSM-5 and ICD-10, or ICD-11, and that terminology and classification systems evolve with medical scientific progress.

The terms "treating", or "treat", or "treatment" are intended to refer to all processes wherein there may be a slowing, interrupting, arresting, controlling, alleviating, stopping, reducing, or reversing the progression or severity of an existing symptom, disorder, condition, or disease, described herein, but does not necessarily indicate a total elimination of all disorder or disease symptoms. Treatment includes administration of a protein or nucleic acid or vector or composition for treatment of a disease, disorder, or condition in a patient, particularly in a human. Treatment includes administration of an antibody of the present disclosure for treatment of a disease or disorder in a human that would benefit from a reduction in epiregulin activity, and includes wherein said treatment provides: (a) inhibiting further progression of the disease, i.e., arresting its development; (b) relieving the disease, i.e., causing regression of the disease or disorder or alleviating symptoms or complications thereof; and/or (c) preventing the onset of the disease of symptoms. Treatment, as defined used herein, expressly includes reducing incidence of pain, ameliorating a pain, or one or more symptoms of a pain, palliating a pain, or one or more symptoms of a pain, delaying the development of pain. Treatment also includes, in some situations, treating the pain, but not necessarily modifying the underlying disease or condition giving rise to the pain. As used herein, "therapy resistant pain" is defined as pain refractory to two or more prior monotherapy and/or dual therapy treatment regimens.

"Reducing incidence" of pain as used herein means any of reducing duration, and/or frequency of pain (including, for example, delaying or increasing time to pain symptoms in an individual). As is understood by those skilled in the art, individuals may vary in terms of their response to treatment. Treatment of pain also includes reducing the severity of the pain as well as reducing the need for and/or amount of (e.g., exposure to) other drugs and/or therapies generally used for this condition, including, for example, opiates. "Ameliorating" a pain or one or more symptoms of a pain (such as osteoarthritis pain) means a lessening or improvement of one or more symptoms of a pain, as compared to not administering an antibody or composition of the present disclosure. "Ameliorating" also includes shortening or reduction in duration of a symptom. "Palliating" a pain or one or more symptoms of a pain (such as osteoarthritis pain) means lessening the extent of one or more undesirable clinical manifestations of pain in an individual, or population of individuals, treated with an antibody or composition in accordance with the present disclosure. As used therein, "delaying" the development of pain means to defer, hinder, slow, retard, stabilize, and/or postpone progression of pain, such as osteoarthritis pain. Such a delay can be of varying lengths of time, depending on the history of the disease and/or individuals being treated. As is evident to one skilled in the art, a sufficient or significant delay can, in effect, encompass prevention, in that the individual does not develop pain. A method that "delays" development of the symptom can be a method that reduces probability of developing the symptom in a given time frame, and/or reduces the extent of the symptoms in a given time frame, when compared to not using the method. Such comparisons are typically based on clinical studies, using a statistically significant number of subjects.

"Effective amount" means the amount of an anti-human epiregulin antibody of the present disclosure, or a pharmaceutical composition comprising such an antibody, that will elicit the biological or medical response of or desired therapeutic effect on a tissue, system, or human, that is being sought by the treating health professional. As used herein, the term "effective response" of a patient or a patient's responsiveness to treatment refers to the clinical or therapeutic benefit imparted to a patient upon administration an antibody of the present disclosure. An effective amount of the antibody may vary according to factors such as the disease state, age, sex, and weight of the individual, and the ability of the antibody to elicit a desired response in the individual. Such desired response includes any one or more of: a decreased level of chronic pain; or improving signs or symptoms of a pain disorder. An effective amount can be readily determined by one skilled in the art, using known techniques, and by observing results obtained under analogous circumstances. An effective amount of an anti-human epiregulin antibody of the present disclosure may be administered in a single dose or in multiple doses. Furthermore, an effective amount of an antibody of the invention may be administered in multiple doses of amounts that would be less than an effective amount if not administered more than once. In determining the effective amount for a patient, a number of factors are considered by the attending medical practitioner, including, but not limited to: the patient's size (e.g., weight or mass), body surface area, age, and general health; the specific disease or disorder involved; the degree of, or involvement, or the severity of the disease or disorder; the response of the individual patient; the particular compound administered; the mode of administration; the bioavailability characteristics of the preparation administered; the dose regimen selected; the use of concomitant medication; and other relevant circumstances known to medical practitioners. A dose (including, but not limited to, subcutaneous, intramuscular, and/or intravenous) can be from about 0.5 mg/kg to about 50 mg/kg. However, doses below or above the doses mentioned herein are also envisioned, especially considering dosage considerations known to those skilled in the art and/or described herein. Progress of the patient being treated may be monitored by periodic assessment, and the dose adjusted accordingly if necessary.

A potential advantage of methods disclosed herein is the possibility of producing marked and/or prolonged relief in a patient suffering from a chronic pain disorder, or with an acceptable safety profile including acceptable tolerability, toxicities and/or adverse events, including anti-drug antibody responses, so that the patient benefits from the treatment method overall. More particularly the antibodies of the present disclosure will provide effective treatment while avoiding clinically undesirable adverse events such as skin rashes (Li T, Perez-Soler R. Skin toxicities associated with epidermal growth factor receptor inhibitors. Target Oncol. 2009 April; 4 (2): 107-19), and or anti-drug antibody responses. The efficacy of the treatment of the present disclosure can be measured by various endpoints that are commonly used in evaluating treatments for various pain disorders. Other approaches to determining efficacy of any particular therapy of the present disclosure can be optionally employed, including, for example, assessments known to the skilled artisan.

BRIEF DESCRIPTION OF THE DRAWINGS

FIG. 5. ELISA assessment of Antibody 1 Fab binding to indicated mutations of epiregulin.

EXAMPLES

Figure 1:
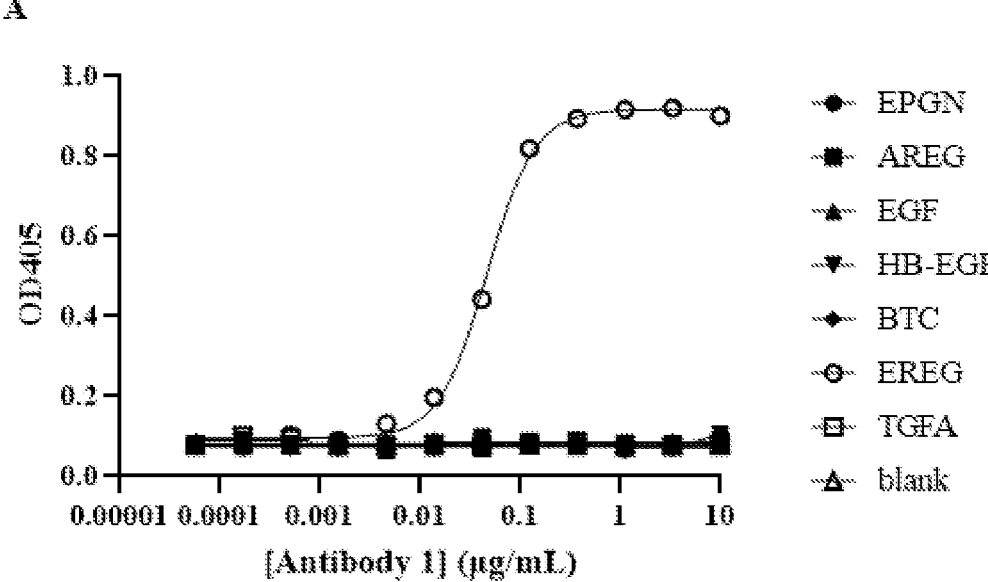
FIG. 1 shows ligand selectivity ELISA results for Antibody 1 (Panel A), and LY 3016859 (Panel B), and demonstrates Antibody 1 selectivity for human epiregulin, but no apparent binding to other EGF family ligands (Epigen, Amphiregulin, Betacellulin, EGF, HB-EGF, and TGFα (TGFA)) as determined in the ligand specificity ELISA described in Example 2. In comparison LY 3016859 binds to both epiregulin and TGFα.
Figure 1:
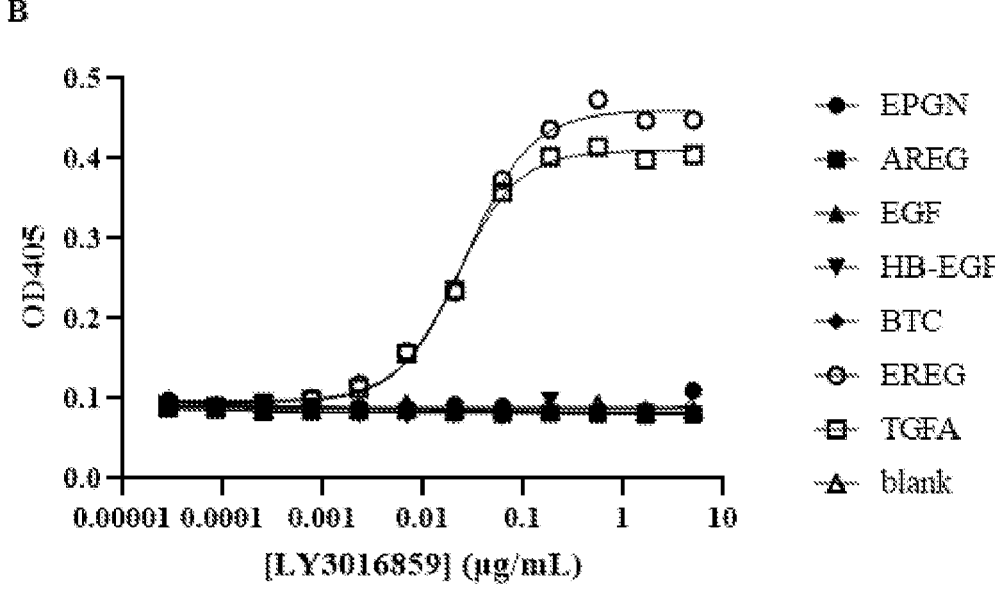

The following examples are offered to illustrate, but not to limit, the claimed invention. The results of the following assays demonstrate that the exemplified monoclonal antibodies and/or antigen-binding fragments thereof of the present disclosure bind and/or neutralize human epiregulin and therefore may be used for treating epiregulin-mediated disorders described herein.

Example 1: Antibody Generation, Expression and Purification

A panel of human anti-epiregulin antibodies is obtained by immunization of a humanized mouse with recombinant EREG (human and cyno) to identify antibodies that could be effective at neutralizing epiregulin signaling. Mutations are systematically introduced into individual complementarity determining regions (CDRs) of each antibody and the resulting libraries are subjected to multiple rounds of selection with decreasing concentrations of antigen, decreased time to associate in antigen, and/or increasing periods of dissociation to isolate clones with improved affinities. The sequences of individual variants are determined and used to construct a combinatorial library which is subjected to an additional round of selection with increased stringency to identify additive or synergistic mutational pairings between the individual CDR regions. Individual combinatorial clones are sequenced, and binding characteristics are determined. This screening can be conducted against human, or mouse epiregulin to increase affinity against one or more selected species (for example Antibody 1 for human epiregulin). Counter-screening can be conducted against other EGFR ligands to maintain selectivity after engineering. Selected antibodies can also be mutagenized to fix post-translational modifications such as methionine oxidation, while retaining binding affinity to epiregulin. Additionally, framework (FW) and CDR substitutions can be made to the antibody to revert these sequences to their germline state in order to reduce potential immunogenicity risk.

Engineered and/or optimized anti-epiregulin antibodies referred to herein as Antibody 1 are obtained, having the amino acid sequences of the variable regions of the heavy chain and light chain, and the complete heavy chain and light chain amino acid sequences, and the nucleotide sequences encoding the same, as listed below in the section entitled "Listing of Amino Acid and Nucleotide Sequences". The SEQ ID NO's corresponding to these sequences are shown in Table 1, as well as the light chain and heavy chain CDR amino acid sequences.

Expression and Purification:

The exemplified anti-epiregulin antibodies of the present disclosure can be expressed and purified essentially as follows. Antibody 1 is expressed in an appropriate host cell, such as HEK293 or CHO, either transiently or stably transfected with an expression system for secreting Antibody 1 using an optimal predetermined HC: LC vector ratio or a single vector system encoding both HC and LC. The expression plasmid contains cDNA versions of the LC and HC genes for Antibody 1 (for example, a DNA sequence of SEQ ID NO: 11 encoding a HC of exemplified Antibody 1 presented in Table 1, and a DNA sequence encoding a LC amino acid sequence according to Table 1, for example, a DNA sequence of SEQ ID NO: 12 encoding a LC of exemplified Antibody 1 presented in Table 1); and are expressed from a commonly-used and suitable construct for this purpose, such as one based on human cytomegalovirus major immediate early promoters.

Medium, into which an antibody of the present invention has been secreted, may be purified by conventional techniques, such as mixed-mode methods of ion-exchange and hydrophobic interaction chromatography. For example, the medium may be applied to and eluted from a Protein A or G column using conventional methods; mixed-mode methods of ion-exchange and hydrophobic interaction chromatography may also be used. Soluble aggregate and multimers may be effectively removed by common techniques, including size exclusion, hydrophobic interaction, ion exchange, or hydroxyapatite chromatography. The product may be immediately frozen, for example at −70° C., refrigerated, or may be lyophilized. Various methods of protein purification may be employed, and such methods are known in the art and described, for example, in Deutscher, Methods in Enzymology 182:83-89 (1990) and Scopes, Protein Purification: Principles and Practice, 3rd Edition, Springer, NY (1994). Antibody 1 may be immediately frozen at −70° C. or stored at 2-8° C. for several months, or may be lyophilized, or preserved in 4° C. for immediate use. Amino acid SEQ ID NOs for exemplified human antibodies of the present invention are shown in Table 1.

Example 2: Characterization of the Anti-Epiregulin Antibodies

Epiregulin regents are made as fusion proteins, cleaved off, and purified. Cleaved epiregulin is the mature soluble form which includes extra amino acids relative to the native form and is used for in vitro binding and neutralization assays (SEQ ID NO's: 14-17). The human epiregulin (EREG) fusion (SEQ ID NO: 19) is also used in the binding assay (capture reagent), and a full length epiregulin sequence (SEQ ID NO: 18) is used for cell-based binding and effector function assays which has a single mutation to reduce shedding.

Mature, soluble epiregulin is expressed as a HRV3C protease cleavable C-terminal fusion on a monomeric human IgG4 Fc (F405Q/Y407E) (SEQ ID NO: 19) in a transiently transfected CHO cell culture. Fusion protein is captured with a Protein A affinity column and is further purified by size exclusion chromatography. The fusion is cleaved with HRV3C protease, flowed through a Protein A affinity column to remove the monomeric Fc, and further purified by size exclusion chromatography to yield mature, soluble epiregulin.

```
Sequences of antigens:
Cleaved human epiregulin
                                (SEQ ID NO: 14)
GPGVSITKCSSDMNGYCLHGQCIYLVDMSQNYCRCEVGYTGVRCEHFFLG Cleaved cynomolgus monkey epiregulin
                                (SEQ ID NO: 15)
GPGVSITKCNSDMNGYCLHGQCIYLVDMSQNYCRCEVGYTGVRCEHFYLG Cleaved rat epiregulin
                                (SEQ ID NO: 16)
GPGVLITKCSSDMDGYCLHGHCIYLVDMSEKYCRCEVGYTGLRCEHFFLG Cleaved rabbit epiregulin
                                (SEQ ID NO: 17)
GPGVSITKCGSDMNGYCLHGQCIYLVDMSENYCRCEVGYTGVRCEHFFLG
```

```
                          -continued
Full length human epiregulin (membrane bound with
T111P mutation)
                                (SEQ ID NO: 18)
MTAGRRMEMLCAGRVPALLLCLGFHLLQAVLSTTVIPSCIPGESSDNCTAL

VQTEDNPRVAQVSITKCSSDMNGYCLHGQCIYLVDMSQNYCRCEVGYTGVR

CEHFFLTVPQPLSKEYVALTVILIILFLITVVGSTYYFCRWYRNRKSKEPK

KEYERVTSGDPELPQV

Monomeric Fc human epiregulin
                                (SEQ ID NO: 19)
APEAAGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWES

NGQPENNYKTTPPVLDSDGSFQLESRLTVDKSRWQEGNVFSCSVMHEALHN

HYTQKSLSLSLGGGGGSGGGGSLEVLFQGPGVSITKCSSDMNGYCLHGQCI

YLVDMSQNYCRCEVGYTGVRCEHFFLG
```

Sequences of mature epiregulin from various species are generally known in the art, and reference sequences are for example as follows: Mature, soluble human epiregulin reference sequence (NP_001423.1 63-108), Mature, soluble cynomolgus monkey (also referred to herein as cyno) epiregulin reference sequence (XP_005555120.1 63-108), Mature, soluble rat epiregulin reference sequence (NP_067721.1 56-101), and Mature, soluble rabbit epiregulin reference sequence (XP_008265968.1 57-102). Other human EGFR ligands reference sequence numbers are: Human TGFa (NP_003227.1), EREG (NP_001423.1), EPGN (NP_001257918.1), AREG (NP_001648.1), BTC (NP_001720.1), EGF (NP_001954.2), HB-EGF (NP_001936.1).

Binding Affinity to Human Epiregulin

The solution phase equilibrium binding affinities of Antibody 1 to human (SEQ ID NO: 14), cynomolgus monkey (SEQ ID NO: 15), rat (SEQ ID NO: 16), and rabbit (SEQ ID NO: 17) epiregulin are measured by an MSD solution equilibrium titration (MSD-SET) assay at 37° C. (See for example Darling R J, Brault P-A (2005) Kinetic Exclusion Assay Technology: Characterization of Molecular Interactions. Assay and Drug Development Technologies 2:647 657.)

An MSD SI6000 instrument (Meso Scale Discovery, Rockville, MD) is used for reading MSD plates. MSD assay plates are prepared as follows. A multi-array 96-well plate (Meso Scale Discovery, P/N L15XA-3) is coated overnight at 2-8° C. with 30 μl of a 1 μg/ml solution of a monomeric Fc-human epiregulin fusion in PBS. Plates are washed 3× in PBST following coating, then blocked for 1 hour at room temperature with shaking in 3% Blocker A (diluted in PBS from 5% Blocker A, Meso Scale Discovery, P/N R93AA-1).

SET samples are prepared in 1% Blocker A at pH 6.0 and at pH 7.4. Antibody is diluted to either 20 and 200 pM (pH 7.4) or 200 pM and 2 nM (pH 6.0). Epiregulin is serially diluted for a total of 12 dilutions centered around 2× the antibody concentration. This is accomplished by using starting concentrations of 10 and 100 nM (pH 7.4) or 100 nM and 1000 nM (pH 6.0) which are then 10× diluted once, 2× serially diluted 9 times, and then 10× diluted for the final dilution. Epiregulin titrations and fixed concentration antibody solutions are combined 1:1 to prepare the SET solutions. SET solutions are incubated at 37° C. for approximately 96 hours to allow binding to reach equilibrium. 100 μl of the SET solution is transferred to the prepared MSD plate in duplicate rows and incubated at room temperature for 10 minutes to capture free antibody. Following incubation, the plate is washed 3× with PBST, then 100 µl of 1 µg/ml biotinylated goat anti-human kappa primary antibody (Southern Biotech, Catalog 2060-08) in 1% Blocker A is added to all wells. This is incubated on a plate shaker at room temperature for 60 minutes. The plate is then washed 3× with PBST, then 100 µl of 1 µg/ml SULFO streptavidin (Meso Scale Discovery, P/N R32AD-1) in 1% Blocker A is added to all wells. This is incubated on a plate shaker at room temperature for 30 minutes. The plate is then washed 3× with PBST, then 100 µl of 1× Read Buffer T (diluted in water from 4× Read Buffer T, Meso Scale Discovery, P/N R93AA-1) is added before reading the plate. Dissociation constant (KD) and a least common multiplier (LCM) ligand correction factor to account for unknown active antigen fraction are globally fit from the MSD-SET data to an equilibrium binding equation using non-linear regression. This is done for each pair of fixed antibody concentrations at a given pH.

At pH 7.4, Antibody 1 binds to human epiregulin with an affinity ($K_D$) of 14.9 pM, to cynomolgus monkey epiregulin with a $K_D$ of 26.8 pM, to rat epiregulin with a $K_D$ of 30.2 pM, and to rabbit epiregulin with a $K_D$ of 24.0 pM. At pH 6.0, Antibody 1 binds to human epiregulin with a $K_D$ of 195 pM, to cynomolgus monkey epiregulin with a $K_D$ of 328 pM, to rat epiregulin with a $K_D$ of 286 pM, and to rabbit epiregulin with a $K_D$ of 330 pM. The pH selectivity of Antibody 1 (pH 6.0 $K_D$/pH 7.4 $K_D$) is 13.0 for human epiregulin, 12.2 for cynomolgus monkey epiregulin, 9.5 for rat epiregulin, and 13.7 for rabbit epiregulin. pH dependent antigen binding can provide improvements in both pharmacokinetics and the duration of target neutralization (See Vincent, K. J. and M. Zurini (2012). "Current strategies in antibody engineering: Fc engineering and pH-dependent antigen binding, bispecific antibodies and antibody drug conjugates." Biotechnol J 7(12): 1444-1450), and Antibody 1 and/or antibodies of the present disclosure exhibit advantageous pH selectivity for epiregulin binding which are conceived to provide useful pharmacokinetic and epiregulin neutralization properties.

TABLE 3

In Vitro Binding Affinities of Antibody 1 to epiregulin measured by MSD-SET at 37° C., at pH 7.4 and 6.0. $K_D$ values are the average ± standard deviation of 3 independent replicates.

| Species | pH 7.4 Affinity (pM) | pH 6.0 Affinity (pM) | Selectivity (pH 6.0 $K_D$/ pH 7.4 $K_D$) |
|---|---|---|---|
| Human | 14.9 ± 2.9 | 195 ± 43 | 13.0 |
| Cynomolgus monkey | 26.8 ± 10.3 | 328 ± 110 | 12.2 |
| Rat | 30.2 ± 15.9 | 286 ± 47 | 9.5 |
| Rabbit | 24.0 ± 7.3 | 330 ± 34 | 13.7 |

Results are reported as the mean of the $K_D$ from 3 independent replicates. Error estimate is calculated as the standard deviation of the independent replicates. The affinity of Antibody 1 to human EREG at pH 7.4 represents an approximate 70-fold improvement in affinity, relative to LY3016859, which may result in a significantly lower dose of Antibody 1 needed to achieve equivalent EREG neutralization in vivo. The ability to use a lower dose of Antibody 1 means that necessary inhibition can be accomplished with less antibody, and as a result the drug product may be amenable to subcutaneous administration, which is clinically important for accessibility, tolerability, compliance, compared to an antibody that requires intravenous dosing. This is particularly advantageous in the context of chronic dosing such as is needed for the chronic pain indications described herein.

Ligand Specificity of Antibody 1:

Specificity of antibody binding to EGF family ligands can be tested by enzyme linked immune sorbent assay (ELISA) and/or other common methods well known to the skilled artisan.

ELISA reagent preparation can be conducted as follows. Ligands tested are human Epigen (R&D 6629-EP-025/CF), epiregulin ((SEQ ID NO: 14) prepared and purified as described herein in Example 2, and/or by methods known in the art), Amphiregulin (R&D 262-AR-100/CF), Betacellulin (R&D 261-CE-010/CF), EGF (R&D 236-EG-200), HB-EGF (R&D 259-HE-050/CF), and TGFα (R&D 239-A-100). Ligands are biotinylated with 10-fold excess biotin using Thermo Pierce Sulfo-NHS-LC-Biotin (A39257) for 2 hours on ice, then frozen at −80° C. in small aliquots for individual use.

ELISA assays can be run as follows. Greiner 96 well high binding plates (650061) are coated overnight at 4° C. with 50 µl/well Neutravidin (Thermo-Pierce 31000) at 1 µg/ml in PBS. The coating solution is removed the next day and 100 µl/well Pierce Blocker Casein (37528) is added and incubated at room temperature for 30 minutes or more to block the plates. After blocking, plates are washed 3 times with PBS plus 0.05% Tween20 to remove residual blocking buffer. Biotinylated ligands are diluted in a separate PCR plate (Eppendorf 951020443) in Pierce Casein Blocker at a constant concentration of 20 nM across 12 wells per ligand with a no antigen control in the last row. Ligands are transferred to blocked assay plate and incubated at room temperature for 1 hour. The assay plate is washed 3 times with PBS plus 0.05% Tween20. The antibody to be tested is serial diluted starting at 5 µg/mL (LY3016859) or 10 µg/ml (Antibody 1) in Pierce Casein Blocker with 1:3 dilutions across the plate (12 wells) with a final volume of 50 µl/well and incubated at room temperature for 1 hour. The assay plate is washed 3 times with PBS plus 0.05% Tween20. Anti-Human Kappa-AP secondary antibody (Southern Biotech 2060-04) is added at 50 µl/well at 1:2000 dilution in PBS plus 0.05% Tween20 and incubated at room temperature for 1 hour. The assay plate is washed 3 times with PBS plus 0.05% Tween20. Finally, 50 µl of pNPP substrate (Sigma-Aldrich N2765) is added and allowed to develop until sufficient color is present and read at 405 nm on a Spectramax Plus 384 plate reader by Molecular Devices.

FIG. 1 illustrates ligand selectivity ELISA results for Antibody 1. Antibody 1 demonstrates selectivity for binding human epiregulin, but no apparent binding to other EGF family ligands Epigen, Amphiregulin, Betacellulin, EGF, HB-EGF, and TGFα, as determined in the above ligand specificity ELISA. The selective and specific binding to epiregulin, and not other EGF family ligands, indicates that Antibody 1 may achieve the desired effects of blocking epiregulin signaling while avoiding clinically undesirable effects of binding to other EGF family ligands, such as TGFα or others. Lack of binding to TGFα may reduce the dose required in order to effectively inhibit epiregulin. This selectivity may avoid undesirable clinical adverse events such as skin rashes which have been observed for pan-EGFR inhibitors.

Physicochemical Attributes:

With respect to therapeutic antibody product attributes, including Chemical Stability, Solubility, and Viscosity, Antibody 1 exhibits a desirable combination of physicochemical attributes for use as a human therapeutic agent.

Stability:

Stability of Antibody 1 is assessed at high concentration (approximately 100 mg/ml) formulated in 5 mM histidine, pH 6.0, plus 280 mM mannitol plus 0.05% (w/v) polysorbate-80. Concentrated samples are incubated for a period of 4 weeks at 5° C. and 35° C. Following incubation, samples are analyzed for percent high molecular weight (% HMW) with size exclusion chromatography (SEC), for fragmentation by capillary electrophoresis (CE-SDS), and for chemical modification (for example deamidation, isomerization, or oxidation) by LC-MS peptide mapping. After 4 weeks at 35° C., Antibody 1 exhibited 4% HMW (change in percentage of high molecular weight) of 0.4%, Δ% fragments (change in percentage of fragments) of 0.6%, and no CDR chemical modifications greater than 0.5%.

Photostability under the same formulation conditions is evaluated by a combined total exposure of 40 watt hour/m$^2$ UV light and 240 klux hour visible light at 25° C. Following incubation, samples are analyzed for % HMW by SEC and for chemical modification by LC-MS peptide mapping. Antibody 1 exhibited Δ% HMW measured by SEC of 6.1% and no CDR chemical modifications greater than 0.7% relative to an unexposed control.

Freeze/thaw stability under the same formulation conditions is evaluated using a 3 repeated slow, controlled temperature cycle which mimics the freeze/thaw conditions of large volumes of bulk drug substance placed at −70° C. Antibody 1 exhibited 4% HMW measured by SEC of 1.0% after the 3 freeze-thaw cycles.

These results indicate Antibody 1 possesses advantageous physical and chemical stability sufficient to facilitate development of solution formulations and use as a therapeutic agent.

Solubility:

Solubility is assessed by concentrating 100 mg of Antibody 1 with a 30 kDa molecular weight cut-off centrifugal filter (for example, Amicon U. C. filters, Millipore, catalog #UFC903024) to a volume of approximately 0.5 ml. The final concentration of the sample was measured by UV absorbance at 280 nm using a Solo VPE spectrophotometer (C Technologies, Inc).

Antibody 1 displays a solubility of greater than or equal to 175 mg/ml in 5 mM histidine pH 6 buffer and greater than or equal to 168 mg/ml in PBS pH 7.4. No phase separation or cryo-precipitation is observed at storage at 5° C. or at −5° C. after 1 week. These results indicate that Antibody 1 exhibits sufficient solubility to enable high concentration dosing.

Viscosity:

Viscosity of Antibody 1 and of LY3016859 are analyzed at 15° C. at an approximate concentration of 125 mg/ml using a VROC Initium (RheoSense). Antibody 1 exhibited a viscosity of 6.4 cP at 133 mg/ml in 5 mM histidine at pH 6 plus 280 mM mannitol, and LY3016859 exhibited a viscosity of 12.2 cP at 132 mg/mL in 5 mM histidine at pH 6 plus 280 mM mannitol. These results indicate that Antibody 1 exhibits reduced viscosity relative to LY3016859, and sufficiently low viscosity to enable high concentration dosing. The ability to use a higher concentration of Antibody 1, in combination with the need for a lower dose, means that necessary effective doses can be accomplished in a smaller volume for delivery, and that means the drug product may be amenable to subcutaneous administration, which is clinically important for accessibility, tolerability, compliance, compared to an agent that must be an antibody that requires intravenous dosing.

Example 3: In Vitro Functional Characterization of the Anti-Human Epiregulin Antibodies Neutralization of Epiregulin In Vitro:

Neutralization of epiregulin activity by antibodies of the present disclosure, such as Antibody 1, may be assessed by one or more of the epiregulin-induced cell-based response assays as described below.

Antibodies of the present disclosure are tested for the ability to neutralize epiregulin activity in two independent functional assays. Neutralization of epiregulin activity by Antibody 1 of the present disclosure may be assessed by one or more cell-based activity assays utilizing downstream signaling pathways of the EGFR family of receptors as described below. Determination of mean half-maximum inhibitory concentration (IC$_{50}$) for neutralization assays (C166-AP1-Luc and TGW-pERK) is calculated in Sigma-Plot or GraphPad Prism. In GraphPad Prism IC$_{50}$ is calculated by running non-linear regression analysis of Log$_{10}$ transformed antibody concentration. For assays run only in duplicate or triplicate over 1 plate, IC$_{50}$ and standard deviation (SD) is determined by calculating IC$_{50}$ for each replicate and SD from averaged IC$_{50}$ of replicates. For analysis of compounds across various plates in duplicate or triplicate, IC$_{50}$ is calculated for each plate and SD determined across plates.

Inhibition of Epiregulin Induced Responses in C166-AP1-Luciferase Functional Assay:

The ability of antibodies of the present disclosure to neutralize human epiregulin-induced luciferase reporter activity can be assessed in C166 cells overexpressing a luciferase reporter driven by AP1 activation (C166-AP1-Luc). C166 cells are an endothelial derived cell line which express all 4 EGFR family of receptors with EGFR expression at highest level. For testing Antibody 1 activity, C166-AP1-Luc cells are grown in growth media [DMEM (Gibco 12430-047), 10% FBS (Gibco 10082147), Anti/Anti (Gibco 15240062) and 2 μg/ml Puro (1000×2 mg/ml Puromycin Dihydrochloride (Calbiochem, Cat #540411)] and dissociated in 0.05% trypsin-PBS and plated at 50,000 cells per 1 ml in tissue culture-treated 96 well plates at 50 μl per well in serum free media (growth media without FBS). Cells are treated with 50 μl of 100 ng/ml (16-18.5 nM) final concentration of epiregulin (human (SEQ ID NO: 14), cyno (SEQ ID NO: 15), rat (SEQ ID NO: 16) and rabbit (SEQ ID NO: 17), as described herein above) and serial dilutions of concentrations of Antibody 1 for 6 hr. Following incubation, cells are lysed for 3 minutes with 100 μl Promega™ One-Glo™ Luciferase solution (Promega™, Cat. #E6120). Luminescence is read on Perkin Elmer Wallace 1420 Victor2™ Microplate Reader. The reduction in relative fluorescence units (RFUs) shown in Table 4 below reflects the ability of Antibody 1 to neutralize epiregulin activity of various relevant species tested including human (SEQ ID NO: 14), cyno (SEQ ID NO: 15), rat (SEQ ID NO: 16) and rabbit (SEQ ID NO: 17)). The IC$_{50}$ value for Antibody 1 in neutralizing human epiregulin is 8.7 nM, SD 2.3, n=5 plates, 2-3 replicates/plate (Table 4). Neutralization across relevant species is demonstrated by testing against cynomolgus (IC$_{50}$ 2.1 nM, SD 0.08, n=3 replicates), rat (IC$_{50}$ 2.5 nM, SD 0.27, n=3 replicates), rabbit (IC$_{50}$ 3.6 nM, SD 0.14, n=3 replicates). Assay validation and reduced IC$_{50}$ of Antibody 1 as compared to LY3016859 (Antibody 1 of WO 2012/138510)

was compared confirmed with neutralization of human epiregulin in this assay with LY3016859 (Table 4). Human, rabbit, cyno and rabbit epiregulin used in these studies were generated as described herein above. LY3016895 was demonstrated to neutralize human epiregulin with $IC_{50}$ of 25.9 nM, SD 11.7, n=8 plates, 2-3 replicates/plate, cynomolgus ($IC_{50}$ 8.6 nM, SD 0.27, n=2 plates, 2-3 replicates/plate), rat ($IC_{50}$ 720 nM, SD 10, n=2 plates 2-3 replicates/plate) and rabbit ($IC_{50}$ 11.0 nM, SD 1.15, n=2 plates, 2-3 replicates/plate). Statistical validation of the epiregulin-induced C166-AP1-Luc assay determined the MSR as 1.24, 95% CI of MSR (MSR=minimal significant ratio) 1.15, 1.43 and potency analysis for Antibody 1 of 8.4+/−1.3. This assay demonstrates in vitro neutralization of epiregulin induced functional cellular responses by Antibody 1, and the ability to inhibit the activity of epiregulin from various species, and the potential for Antibody 1 neutralizing effects against epiregulin in vivo.

TABLE 4

| Antibody 1 neutralization of epiregulin induced luciferase reporter activity in C166-AP1-Luciferase cells. | | |
|---|---|---|
| | Antibody 1 $IC_{50}$ ± SD (nM) | LY3016859 $IC_{50}$ ± SD (nM) |
| Human epiregulin | 8.7 ± 2.3 | 25.9 ± 11.4 |
| Cyno epiregulin | 2.1 ± 0.1 | 8.6 ± 0.3 |
| Rat epiregulin | 2.5 ± 0.3 | 720 ± 10 |
| Rabbit epiregulin | 3.6 ± 0.1 | 11.0 ± 1.2 |

For neutralization against human epiregulin mean average and SD was determined by averaging $IC_{50}$ from replicates across 5 plates for Antibody 1 and 8 plates for LY3016859. For neutralization against rat, cyno and rabbit epiregulin $IC_{50}$ from triplicates from 1 plate for each species was averaged and SD determine for Antibody 1. For neutralization against rat, cyno and rabbit epiregulin $IC_{50}$ was generated from averaging $IC_{50}$ from duplicates across 2 different plates for LY3016859.

The data in Table 4 demonstrate that Antibody 1 can effectively neutralize human epiregulin-induced luciferase reporter activity in the above C166-AP1-Luc cell-based assay ($IC_{50}$=8.7 nM), with an approximately 3-fold lower $IC_{50}$ than LY3016895 ($IC_{50}$=25.9 nM). Cross-reactivity to relevant species of epiregulin was confirmed by testing neutralization against rat ($IC_{50}$=2.5 nM), cyno ($IC_{50}$=2.1 nM) and rabbit ($IC_{50}$=3.6 nM) epiregulin. These data support the ability of Antibody 1 to neutralize human epiregulin mediated signaling and treat human diseases in which epiregulin-mediated signaling contributes to etiopathogenesis, such as pain disorders, and in particular OA, DPNP, and CLBP.

Selectivity of Antibody 1 to Epiregulin Neutralization in C166-AP1-Luc Assay:

Selectivity of Antibody 1 for neutralizing epiregulin can be further demonstrated by testing the activity of all 7 EGFR ligands (Epigen, TGFα, BTC, EGF, HB-EGF, epiregulin, and amphiregulin) in the C166-AP1-Luc assay (ligands can be purchased for example from R&D systems: epiregulin #1195-EP-CF, betacellulin #261-CE-CF, EGF #236-EG-CF, TGFα #239-A-CF, HB-EGF #259-HE-CF, Epigen #6629-EP-CF and amphiregulin #262-AR-CF). These 7 EGFR ligands demonstrate AP1 activation with a 2-5 fold increase in luciferase activity, depending on the ligand. The $EC_{50}$ for EGFR ligands is determined by running dose responses of each ligand in C166-AP1-Luc cell line as described herein above. Ligand concentration for stimulation is determined by using the $EC_{50}$-$EC_{80}$ for each ligand (betacellulin 0.8 nM, EGF 1.3 nM, TGFα, 2.5 nM, HB-EGF 0.52 nM, epiregulin 16 nM, Epigen 333 nM and amphiregulin 181 nM, Epigen and amphiregulin were estimated EC50 due to lack of plateau on curve). Antibody 1 demonstrates the ability to neutralize epiregulin-induced luciferase activity in C166-AP1-Luc cells with $IC_{50}$ of 8.7 nM, and in contrast, fails to demonstrate inhibition of betacelluin, EGF, TGFα, HB-EGF, Epigen or amphiregulin-induced luciferase activity in C166-AP1-Luc assay (see Table 5 below). The data in Table 5 also support the pharmacological selectivity of Antibody 1 as specifically neutralizing the activity of epiregulin, but not other family members betacellulin, EGF, TGFα, HB-EGF, Epigen and amphiregulin. This selectivity is important in that Antibody 1 is expected to intervene selectively in epiregulin responses, and thus avoid possible adverse effects that could arise by less specific agents such as LY3016859 that may block other EGFR ligands.

TABLE 5

| Specificity of Antibody 1 in neutralizing epiregulin in a C166-AP1-Luc assay. All 7 EGFR ligands are tested for $EC_{50}$ calculation in a C166-AP-Luc assay. NA (no activity) indicates lack of an inhibition curve to determine an $IC_{50}$ and thus lack of neutralization at highest concentration of antibody tested, 200 nM. For epiregulin neutralization an $IC_{50}$ was calculated using an epiregulin reagent (SEQ ID NO. 22). | | |
|---|---|---|
| | Ligand $EC_{50}$ nM | Antibody 1 $IC_{50}$ nM |
| betacellulin | 0.8 | NA |
| EGF | 1.3 | NA |
| TGFα | 2.5 | NA |
| HB-EGF | 0.13 | NA |
| epiregulin | 7.8 | 8.7 |
| Epigen | 429 | NA |
| amphiregulin | 42.9 | NA |

Ability of Antibody 1 to Neutralize the Epiregulin Induced Responses in a TGW Neuroblastoma Cell Line:

Epiregulin neutralization is further assessed by measuring epiregulin-induced ERK phosphorylation in the TGW neuroblastoma cell line. TGW cells express all 4 of the EGFR family of receptors with EGFR expression being the highest level. In this assay, TGW cells are grown on collagen 1 coated plates in growth media [DMEM High Glucose with NAPYR (Gibco #11995-065), 1×NEAA (Gibco #11140-050), Glutamax (Gibco #35050-061) and 1× Anti-Anti (Gibco #15240-062)]. Cells are dissociated in 0.05% trypsin-PBS and plated in serum free media (growth media with FBS replaced with 0.1% BSA) at 100,000 cells/100 μl in 96-well collagen 1 coated 96-well plates (Corning #354407). In TGW cells, epiregulin treatment (80 ng/ml for 5 minutes) induces over 5-fold increased phosphorylation of ERK (Meso Scale Diagnostics, LLC phospho-ERK1/2 Whole Cell Lysate Kit #K151DWD) as compared to unstimulated cells. Phospho-ERK activation is determined by chemiluminescent induction and displayed as relative fluorescent unites (RFUs). Neutralization of Antibody 1 is determined by incubation of human epiregulin with Antibody 1 in serial dilutions for 20 minutes prior to stimulation of cells. Data is obtained by reading plates on Meso Scale Diagnostics SECTOR Imager. The reduction in epiregulin induced phosphor-ERK1/2 signal with Antibody 1 treatment is shown in Table 6 and reflects the ability of Antibody 1 to neutralize human epiregulin. The $IC_{50}$ value for Antibody 1 in neutralizing human epiregulin induced pERK induction in TGW cells is observed to be 3.4 nM, SD 0.7, (n=2 replicates), which is lower than LY3016859, with an $IC_{50}$ of 14.6 nM, SD 0.7, (n=2 replicates). The data in Table 6 provide evidence of the ability of the Antibody 1 to block human epiregulin-induced phosphor-ERK1/2 activation in TGW cells. This data demonstrates the ability of the antibodies of the present disclosure, and Antibody 1 in particular, to neutralize human epiregulin utilizing two different cell lines with independent readouts and supports the therapeutic use of these antibodies in the treatment of epiregulin mediated disorders, such as chronic pain disorders.

TABLE 6

| Antibody 1 neutralizes the effect of human epiregulin induced phopho-ERK induction in TGW cells. | | |
| --- | --- | --- |
| | Antibody 1 $IC_{50} \pm SD$ (nM) | LY3016859 $IC_{50} \pm SD$ (nM) |
| Human epiregulin | 3.4 ±0.7 | 14.6 ± 0.7 |

Example 4: In Vivo Functional Characterization of Epiregulin in Induced Tactile Allodynia in CD-1 Mice The ability of biologically active molecules epiregulin and TGFα to induce tactile allodynia can be assessed in male CD-1 mice following intraplantar injection. Mice are allowed to acclimate in a temperature and light controlled animal facility with ad libitum water and food for a period of at least 7 days prior to experimentation. On the testing days, animals are brought to the testing room, acclimate for 20 minutes in home cage prior to placing in clear plastic chambers on an elevated metal mesh floor and allowed to acclimate for one hour. Paw withdrawal responses to mechanical stimulations are determined by using calibrated von Frey filaments applied to the plantar surface of hind paw from underneath the cage through openings in the metal mesh floor. The measurements are accomplished with the use of von Frey filaments in an up-down testing paradigm. The force range of eight graded filaments is 0.04 g to 6 g. The paw withdrawal threshold is measured and calculated. Animals are randomized based on baseline value of paw withdrawal threshold to dosing groups, PBS, epiregulin 30 ng, epiregulin 300 ng, TGFα 30 ng, or TGFα 300 ng (murine epiregulin (SEQ ID NO: 20), and murine TGFα (SEQ ID NO: 21) reagents prepared as described herein, or for TGFα as His tagged and purified by standard chromatography techniques (immobilized metal ion affinity chromatography or IMAC followed by size exclusion chromatography or SEC). Then, animals receive hind paw intraplantar injection with 20 μl solution of PBS, or fresh diluted epiregulin or TGFα. Paw withdrawal thresholds are assessed at post-injection 2-hour and 4-hour time points. Data are shown in Table 7 below.

TABLE 7

| | Paw Withdrawal Threshold (g) mean ± SEM (n) | | |
| --- | --- | --- | --- |
| | Baseline | 2 hrs | 4 hrs |
| Vehicle | 2.55 ± 0.50 (10) | 2.34 ± 0.36 (10) | 2.27 ± 0.49 (10) |
| 30 ng epiregulin | 2.58 ± 0.46 (10) | 1.91 ± 0.32 (10) | 1.56 ± 0.34 (10) |
| 300 ng epiregulin | 2.58 ± 0.47 (10) | 1.05 ± 0.49 (10) | 1.32 ± 0.47 (10) |

TABLE 7-continued

| | Paw Withdrawal Threshold (g) mean ± SEM (n) | | |
| --- | --- | --- | --- |
| | Baseline | 2 hrs | 4 hrs |
| 30 ng TGFα | 2.57 ± 0.49 (10) | 2.50 ± 0.52 (10) | 3.13 ± 0.50 (10) |
| 300 ng TGFα | 2.61 ±0 .50 (10) | 2.67 ± 0.53 (10) | 2.40 ± 0.63 (10) |

The effect of epiregulin as compared to TGFα are shown in Table 7 above, and indicate that in this pain model, epiregulin induces a painful response as indicated by a reduction in withdrawal threshold, whereas TGFα does not. Antibody 1 is believed to embody a more selective and specific pain therapeutic as compared to LY3016859 which recognizes both epiregulin and TGFα, and the lack of binding to TGFα by Antibody 1 of the present disclosure is considered to be advantageous with respect to avoiding off target effects, reducing immunogenicity, and improving or lowering the dose which may be needed for therapeutic uses.

Example 5: Characterization of Antibody 1 Immunogenicity Potential

Antibody 1 represents an improved therapeutic antibody in several combined respects, including enhanced affinity for human epiregulin, improved specificity for epiregulin relative to other EGFR ligands, and as compared to LY3016859, improved biophysical properties, and a fully human sequence, the latter of which is believed to provide reduced immunogenicity potential, as supported by the following findings.

Dendritic Cell (DC) Internalization Assay
Monocyte-Derived DC Culturing (MDDC)

CD14+ monocytes are isolated from periphery blood mononuclear cells (PBMCs) and are cultured and differentiated into DC following standard protocols. Briefly, PBMCs are isolated using density-gradient centrifugation with Ficoll (#17-1440-02, GE Healthcare) and Sepmate 50 (#15450, STEMCELL Technologies) from LRS-WBC. CD14+ monocytes are isolated using positive selection with a CD14+ microbead kit (#130-050-201, Miltenyi Biotec) following the manufacturer's manual. Cells are then cultured at 1 million/ml with 1000 unit/ml GM-CSF and 600 unit/ml IL-4 for 6 days to drive to immature dendritic cells (MDDC) in RPMI medium with L-glutamine and 25 mM HEPES supplemented with 10% FBS, 1 mM sodium pyruvate, 1× penicillin-streptomycin, 1× non-essential amino acids, and 55 μM 2-mercaptoethanol (hereafter referred to complete RPMI medium or medium, purchased from Life Technologies). The medium is changed twice, on day 2 and day 5. On day 6, cells are gently collected with a cell scraper and used for experiment. MDDC are characterized visually for dendritic morphology by microscope and for expression of CD14, CD11c, and HLA-DR by flow cytometry. Their ability to respond to LPS treatment is confirmed by measuring upregulation of CD80, CD83, and CD86 using flow cytometry.

Conjugation of Fab-TAMRA-QSY7

A F(ab')2 fragment goat anti-human IgG (Jackson ImmunoResearch) is double-labeled with QSY7-NHS and TAMRA-SE (Molecular Probes) to obtain Fab-TAMRA-QSY7 used as a universal probe to track test article internalization. Each vial of F(ab')2 (approximately 1 ml at 1.3 mg/ml) is concentrated to about 2 mg/ml by centrifugation at 14,000 rcf for 2 minutes with the Amico Ultra-0.5 centrifugal filter device (#UFC501096, Millipore). The pH is adjusted to basic (>pH 8) with 10% (v/v) 1 M sodium bicarbonate, and 6.8 µl QSY-NHS stock solution at 10 mM in DMSO is added and mixed. The reaction vial is kept in dark at room temperature for 30 min. The intermediate product, Fab-QSY7, is purified with Zeba Spin desalting column (#89890, Thermo Scientific) by centrifugation at 1000 relative centrifugal force (RCF) for 2 min. The concentration and degree of labeling (DOL) are calculated by measuring the absorbance at 280 nm and 560 nm on a NanoDrop (ThermoFisher). Fab-QSY7 is then concentrated to about 2 mg/ml by centrifugation at 14,000 rcf for 2 min with Amico Ultra-0.5 centrifugal filter device again. After pH adjustment with 10% (v/v) 1 M sodium bicarbonate, 4.3 µl of 15 mM TAMRA-SE stock solution in DMSO are added and mixed. After 30 min. at room temperature in the dark, the final product Fab-TAMRA-QSY7 is purified and collected using a Zeba Spin desalting column by centrifugation at 1000 rcf for 2 min. The concentration and DOL are again quantitated by reading the absorbance at 280 nm, 555 nm, and 560 nm on a NanoDrop Spectrophotometer. Using this protocol, about 300 µl of Fab-TAMRA-QSY7 at around 1.5 mg/ml with approximately two QSY7 and two TAMRA per F(ab')2 are obtained.

Standardized Internalization Study by FACS

Individual test molecules are normalized to 1 mg/ml with PBS and then further diluted to 8 µg/ml in complete RPMI medium. Fab-TAMRA-QSY7 is diluted to 5.33 µg/ml in complete RPMI medium. The antibody and Fab-TAMRA-QSY7 are mixed with equal volume and incubated for 30 min at 4° C. in dark for complex formation. MDDC are resuspended at 4 million/ml in complete RPMI medium and seeded at 50 µl per well in a 96-well round-bottom plate, to which 50 µl of the antibody/probe complex is added. Cells are incubated for 24 h at 37° C. in a $CO_2$ incubator. Cells are washed with 2% FBS PBS and resuspended in 100 µl 2% FBS PBS with Cytox Green live/dead dye. Data are collected on a BD LSR Fortessa X-20 and analyzed in FlowJo. Live single cells are gated and percent of TAMRA fluorescence positive cells is recorded as the readout.

Data Presentation and Statistical Analysis

Molecules are tested on three or more donors in duplicate or triplicate. The percent of TAMRA-positive population is considered for each donor. To allow the comparison of molecules with data generated from different donors, a normalized internalization index (NII) is used. The internalization signal is normalized to IgG1 isotype (NII=0) and an internal positive control PC (NII=100) using the formula:

$$100 \times \frac{X_{TAMRA} - IgG1\ isotype_{TAMRA}}{PC_{TAMRA} - IgG1\ isotype_{TAMRA}}$$

where $X_{TAMRA}$, IgG1 isotype$_{TAMRA}$, and $PC_{TAMRA}$ are the percent of TAMRA-positive population for the test molecule X, IgG1 isotype, and PC respectively. Data are analyzed in JMP® 14.1.0 or Graphpad Prism 8.1.2. Mean of the percent of TAMRA-positive population and NII are calculated and reported. Increased internalization in antigen presenting cells such as DCs is associated with increased immunogenicity risk. Results in Table 9 demonstrate decreased DC internalization of Antibody 1 relative to LY3016859, and therefore a decreased immunogenicity risk.

28

TABLE 9

| DC internalization Results | | |
|---|---|---|
| Test Antibody | % TAMRA+ | NII |
| LY3016859 | 10.3 | 16.9 |
| Antibody 1 | 2.3 | 1.3 |

(See e.g. Wen, Y., Cahya, S., Zeng, W. et al. Development of a FRET-Based Assay for Analysis of mAbs Internalization and Processing by Dendritic Cells in Preclinical Immunogenicity Risk Assessment. *AAPSJ* 22, 68 (2020))

MAPPS Assay (MHC-Associated Peptide Proteomics) Methods:

Primary human dendritic cells from 10 normal human donors are prepared from buffy coats by isolation of CD-14 positive cells and differentiated into immature dendritic cells by incubation with 20 ng/ml IL-4 and 40 ng/ml GM-CSF in complete RPMI media containing 5% Serum Replacement (Thermo Fisher Scientific, cat #A2596101) for 3 days at 37° C. and 5% $CO_2$ as described (Knierman et al., "The Human Leukocyte Antigen Class II Immunopeptidome of the SARS-COV-2 Spike Glycoprotein", Cell Reports, 33, 108454 (2020)). Three micromolar of test antibody is added to approximately $5\times10^6$ cells on day 4 and fresh media containing 5 mg/ml of LPS to transform the cells into mature dendritic cells is exchanged after 5-hour incubation. The matured cells are lysed in 1 ml of RIPA buffer with protease inhibitors and DNAse the following day. The lysates are stored at −80° C. until sample analysis.

An automated liquid handling system is used to isolate the HLA-II molecules from thawed lysate using biotinylated anti-pan HLA class II antibody (clone Tu39). The bound receptor-peptide complex is eluted with 5% acetic acid, 0.1% TFA. The eluted MHC-II peptides are passed over a prewashed 10 k MWCO filter to remove high molecular weight proteins. The isolated MHC-II peptides are analyzed by nano LC/MS using a Thermo easy 1200 nLC-HPLC system with a Thermo LUMOS mass spectrometer. The separation used a 75 µm×7 cm YMC-ODS C18 column for 65-minute gradient with a 250 nL/min flow rate and 0.1% formic acid in water as A solvent and 80% acetonitrile with 0.1% formic acid as B solvent. Mass spectrometry is run in full scan mode with 240,000 resolution followed by a 3 second data dependent MS/MS cycle comprised of ion trap rapid scans with HCD and EThcD fragmentation.

Peptide identifications are generated by an internal proteomics pipeline (Higgs et al., "Label-free LC-MS method for the identification of biomarkers", Methods in Molecular Biology, 428, 209-230 (2008)) using multiple search algorithms with no enzyme search parameter against a bovine/human database containing the test antibody sequences. A KNIME workflow is used to process the identification files for the samples. Peptides identified from the test articles are aligned against the parent sequence. A summary is created for all donors that annotates the percent of donors that display non-germline residues, the number of different regions that display peptides with non-germline residues and the depth of peptide display at each region with non-germline residues. Increases in the extent of display of non-germline peptides is associated with increased risk for immunogenicity. Results in Table 8 show decreased display of non-germline peptides for Antibody 1 compared to LY3016859, and therefore a decreased risk of immunogenicity for Antibody 1.

TABLE 8

MAPPs Results

| Test Antibody | % Donors | # of clusters | Total # of non-germline residues from all clusters | Total # of non-germline peptides from all clusters |
|---|---|---|---|---|
| LY3016859 | 60% | 3 | 15 | 20 |
| Antibody 1 | 20% | 2 | 5 | 5 |

Example 6. Demonstration of Binding to Membrane Epiregulin In Vivo after Dosing In Rats Epiregulin exists in both a membrane bound form, and a soluble form that occurs with cleavage of the membrane form by ADAM (A disintegrin and metalloprotease) proteases. The ability of antibodies of the present disclosure to bind to the membrane form of epiregulin in vivo after peripheral dosing, for example by subcutaneous injection, may be assessed by ex vivo isolation of tissue followed by adaptation of standard immunofluorescent staining methods as described herein and/or known to the skilled artisan. Positive and specific immunofluorescent labelling of the epithelial layer of the rat tongue can be demonstrated with Antibody 1.

Rat tongue can be obtained from euthanized Male Sprague Dawley rats (weighing 140-215 grams) after various doses (0.1 to 100 mg/kg, subcutaneous) of antibodies to be tested including Antibody 1, or control or comparator antibodies, and at various times after dosing (3-28 days after dosing), and flash frozen on dry ice. Frozen coronal 20 micron sections of tongue tissue are thawed, washed in PBS for 3 minutes, and fixed in 4% paraformaldehyde for 10 minutes. Slides are washed in Super Sensitive Wash Buffer (HK583-5K, Biogenex) and then blocked with Power block (HK065-5K, Biogenex) plus 0.1% Triton x-100 for 10 minutes. Slides are then washed and incubated for 15 minutes at room temperature with Alexa Fluor 488 goat anti-human IgG (A11013, Life Technologies, 13.3 μg/ml), and a labeled human/mouse IgG1 chimera, referred to herein as "Antibody 1 VR chimera" (SEQ ID's 53 and 54), having the variable regions (SEQ ID's 3 and 4) of Antibody 1 and murine constant regions (DyLight 650 labeled). Slides are washed 3 times and Prolong gold antifade reagent applied prior to coverslips. The fluorescent images at 488 and 650 nm wavelength from each animal are captured utilizing a Keyence BZ800 using the same exposure settings for all images. The green or red signal within the positively stained epithelial layer is quantified utilizing the ImageJ-Win64 software for average intensity by taking four random areas of interest. The green signal arises from bound Antibody 1, or control antibody, or reference comparator antibody (dosed in vivo), and the red signal is unbound epiregulin, where the detection antibody competes with bound drug, and only stains free epiregulin and not bound. Resulting data are normalized by utilizing the ratio of Alexa Fluor 488 goat anti-human IgG signal (green) over the remaining Antibody 1 VR chimera signal (red).

Figure 2:
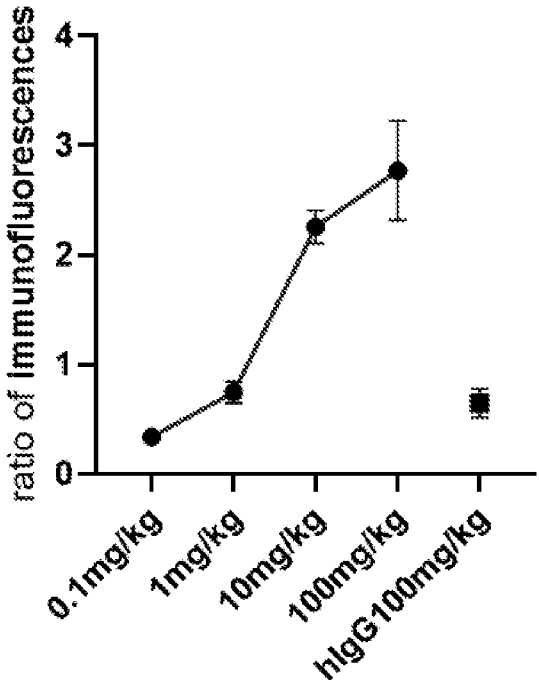
FIG. 2. Binding of membrane epiregulin in vivo 3 days after administration of Antibody 1 (filled circles) compared to a control hIgG antibody (filled square).
Figure 3:
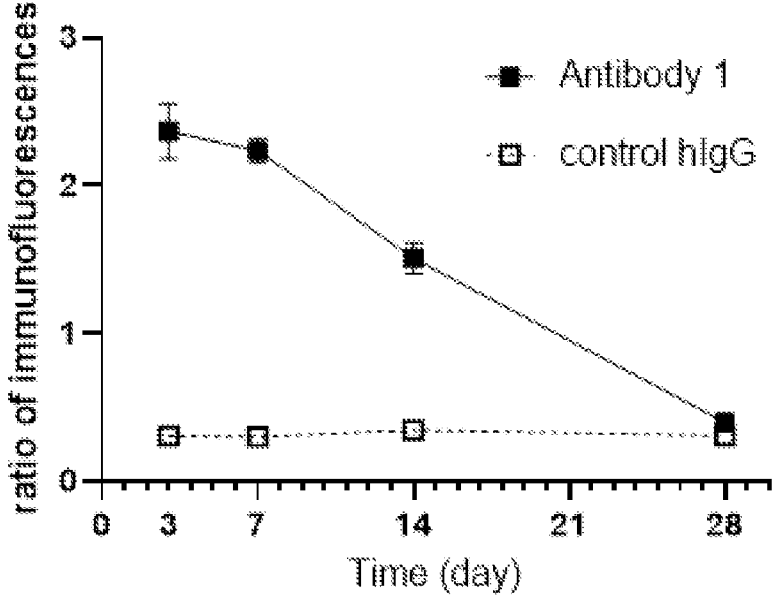
FIG. 3. Pretreatment time dependent binding of membrane epiregulin in vivo following a 10 mg/kg subcutaneous dose of Antibody 1 (filled squares) compared to a control hIgG antibody (open squares).
Figure 4:
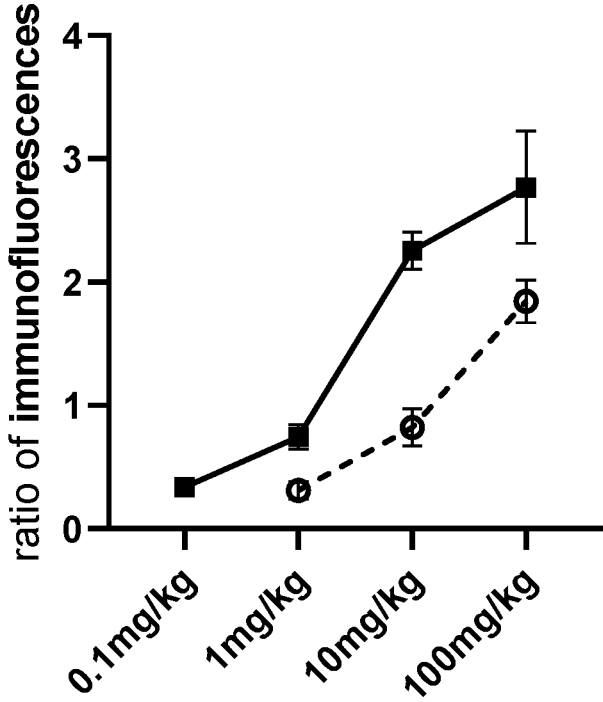
FIG. 4. Binding of membrane epiregulin in vivo 3 days after administration of Antibody 1 (filled squares) compared to a >50× less potent epiregulin binding comparator antibody (open circles).

FIG. 2 shows that 3 days after dosing with Antibody 1, at doses ≥1 mg/kg, a significant dose dependent increase in binding of membrane epiregulin is observed in vivo. FIG. 3 shows that after a single dose of 10 mg/kg of Antibody 1, there is a sustained binding of membrane epiregulin in vivo for at least 14 days. FIG. 4 demonstrates a higher degree of bound membrane epiregulin in vivo, for Antibody 1, compared to a >50x less potent epiregulin binding comparator antibody. FIG. 4 shows the improvements in Antibody 1 affinity also translate to improved membrane-bound epiregulin ligand binding in vivo.

Example 7: Epitope Mapping of Antibody 1

Antibody 1 is a human IgG4 antibody that selectively binds and neutralizes the EGFR ligand family member epiregulin (EREG) with high affinity, and selectivity with respect to other EGFR ligand family members, and advantageous epiregulin neutralizing activity and pharmacokinetic properties. These properties, along with additional stability and viscosity and solubility properties described herein, result in an antibody with a combination of improved attributes and an advantageous therapeutic agent to neutralize EREG activity. Epitope mapping studies were performed to determine the specific amino acids in human EREG required for Antibody 1 binding and specificity. Critical amino acids were identified from the crystal structure of the Antibody 1 Fab/EREG complex, and contribution of these amino acids were further characterized through mutagenesis and binding studies. The contributions of these amino acids provide a structural basis for the specificity of Antibody 1 for EREG as compared to other EGFR ligand family members. These results also inform the cross-reactivity and selectivity in relevant pre-clinical species.

Sequences for test materials are provided in the Listing of Amino Acid and Nucleotide Sequences and cross-referenced as follows: Human EREG (SEQ ID NO: 13), Antibody 1 Fab HC (SEQ ID NO: 51), Antibody 1 Fab LC (SEQ ID NO: 52), Mono Fc human EREG (SEQ ID NO: 19), Mono Fc human EREG E95H (SEQ ID NO: 46), Mono Fc human EREG E95A (SEQ ID NO: 45), Mono Fc human EREG H78N (SEQ ID NO: 44), Mono Fc human EREG H78A (SEQ ID NO: 43), Mono Fc human EREG F106K (SEQ ID NO: 50), Mono Fc human EREG F106A (SEQ ID NO: 49), Mono Fc human EREG Y98A (SEQ ID NO: 47), Mono Fc human EREG L77F (SEQ ID NO: 42), Mono Fc human EREG R102A (SEQ ID NO: 48).

Antibody 1 Fab fragment and human EREG were both produced in transient CHO expression and purified by standard techniques. Complex was prepared by adding 30% molar excess of EREG to Antibody 1 Fab, then purified by size exclusion chromatography to remove excess free EREG. Antibody 1 Fab binding to EREG was first probed by Western blot analysis and showed that Antibody 1 Fab can recognize the denatured, non-reduced, but not the denatured, reduced EREG in this assay. This strongly suggests a conformational epitope dependent on the EREG disulfide bonds.

Crystal Structure of the Fab Fragment of Antibody 1 Bound to Human Epiregulin

The crystal structure of the Fab fragment of Antibody 1 bound to human epiregulin was solved. The complex was crystallized and the 1.8 Å structure was solved by molecular replacement using Phaser 2.8.3 and subsequently refined with Refmac 5.8.0258. In the crystal, Antibody 1 Fab's bind on opposite faces of an epiregulin dimer. The epiregulin Leu77 and His78 sidechains are at the center of the epitope with Leu77 buried in a hydrophobic pocket and His78 sidechain centered in a network of hydrogen bonds. The Antibody 1 heavy chain Arg50 sidechain is a hydrogen bond donor to the heavy chain Tyr52 sidechain hydroxyl, the heavy chain Tyr52 sidechain hydroxyl is a hydrogen bond donor to the deprotonated His78 sidechain $N^{\delta 1}$ hydrogen bond acceptor, the protonated His78 sidechain $N^{\varepsilon 2}$ is as a hydrogen bond donor to a water molecule, and this water molecule is as a hydrogen donor to the heavy chain Leu109 and light chain Tyr107 backbone carbonyls. Antibody 1 residues are numbered by IMGT convention. Additional identified epitope contacts include Glu95, Tyr98, Arg102, and Phe106 sidechains and Leu77, Val96, and Glu104 backbone. The structure clearly demonstrates that the Antibody 1 epitope is conformational and not linear, confirming the Western results above.

Mutant Epiregulin ELISA with Antibody 1 Fab

Key epitope residues were further characterized by point mutagenesis to understand their relative contribution both to binding and to selectivity. Mono Fc EREG fusions (see above) were diluted to 1 µg/mL in PBS, and 100 µL was added to each well to coat an ELISA plate (Greiner Cat #655061) overnight at 5° C. Variants were grouped by column on the plate with wild type coated in 3 replicate columns and the point mutants coated in single replicate columns. Following the coat, the plate was washed 3×200 µL per well with PBST, then blocked at RT for 1 hour on a plate shaker using casein blocking buffer (Thermo Cat #37528). After blocking, the plate was washed as before. Antibody 1 Fab fragment was diluted to 1 µg/mL in casein blocking buffer, then 3× serially diluted in blocking buffer for a total of 7 concentrations and a blocking buffer blank. The Fab dilution series was added to the prepared ELISA plate, 100 µL per well, and incubated at RT for 1 hour on a plate shaker. The plate was washed as before, then 100 µL of goat anti-human kappa HRP secondary (Southern Biotech Cat #2060-05) diluted 1:8,000 in blocking buffer was added to each well. The plate was incubated with secondary antibody for 1 hour at RT on a plate shaker, then washed as before. TMB substrate was prepared (Thermo Cat #34021), and 100 µL was added to all wells. Plate was incubated statically at RT for 3-5 minutes, then 100 µL of 1N HCl was SPR Analysis of Antibody 1 Fab Fragment Binding to Mono Fc Human EREG Mutants A Biacore 8K instrument and reagents (Cytiva) were used for the SPR analysis of Antibody 1 Fab fragment binding to both mono Fc human EREG mutants. Low levels of mono Fc human EREG mutants were immobilized in the sample flow cells (Fc2) of a CM5 S series sensor chip (Cytiva P/N BR100530) using an amine coupling kit (Cytiva P/N BR 100050) and the "Low Level CM5 Coupling" method in Biacore 8K control software. Running buffer was 1×HBS-EP+pH 7.4 (prepared from 20×HBS-EP+, Teknova P/N H8022) or 1×MBS-EP+pH 6.0 (10 mM MES+150 mM NaCl+3 mM EDTA+0.05% Tween 20), and running temperature was 37° C. Biacore experiments were performed in three independent experiments with single replicates of each dilution within each independent experiment. Reference subtracted, blank subtracted SPR data was analyzed using either the '1:1 binding' kinetic model (EREG variants) or the 'Steady State Affinity' models with Biacore Insight Evaluation Version 3.0 (Cytiva) to determine a $K_D$ value.

Antibody 1 Fab was diluted in running buffer to 300 nM (pH 7.4), or 900 nM (pH 6.0), then 3× serially diluted down for a total of 7 dilutions. Fab was injected over all flow cells for 240 seconds followed by an 1800 second dissociation at a flow rate of 50 µL/min. Chip surface was regenerated with 2×30 second injections of 7M guanidine at 100 µL/min. Reference subtracted data was collected as sample flow cell minus reference flow cell (Fc2-Fc1) in each of the 8 channels, and then the reference subtracted data was buffer blank subtracted.

Binding affinity of a subset of the mutants was measured by Biacore at 37° C. Results are reported in Table 9 as the mean±standard deviation of 3 independent replicate measurements. "rel" indicates relative to wild type (wt).

TABLE 9

| Antibody 1 binding affinity to wild type and mutant EREG at pH 6.0 and pH 7.4 at 37° C. | | | | | | |
|---|---|---|---|---|---|---|
| EREG Variant | SEQ ID NO | pH 7.4, 37° C. $K_D$ (pM) | pH 7.4 $K_D$ Fold Change (rel to wt) | pH 6.0, 37° C. $K_D$ (pM) | pH 6.0 $K_D$ Fold Change (rel to wt) | $K_D$ pH 6.0/$K_D$ pH 7.4 |
| wt (wild type) | 27 | 51.8 ± 5.6 | 1 | 508 ± 6 | 1 | 9.8 |
| L77F | 53 | 26,500 ± 1,600 | 511 | 197,000 ± 6,000 | 388 | 7.4 |
| H78N | 55 | 29,300 ± 1,500 | 565 | 25,600 ± 2,200 | 50 | 0.9 |
| E95A | 56 | 19,600 ± 1,700 | 379 | 81,400 ± 500 | 160 | 4.2 |
| E95H | 57 | 7,180 ± 420 | 139 | 47,300 ± 700 | 93 | 6.6 |
| R102A | 59 | 177 ± 43 | 3 | 1,930 ± 140 | 4 | 10.9 |
| F106A | 60 | 12,500 ± 500 | 241 | 77,100 ± 3,600 | 152 | 6.2 |
| F106K | 61 | 54,600 ± 3,100 | 1,050 | 293,000 ± 16,000 | 577 | 5.4 | added to all wells to stop the reaction. The plate was read at 450 nm on a plate reader. Blank subtracted ELISA data were plotted in GraphPad Prism 9 with antibody concentration on the X-axis and OD450 on the Y-axis. Curves were generated by fitting the data using non-linear regression to the 'Sigmoidal, 4PL, X is concentration' model.

Figure 5:
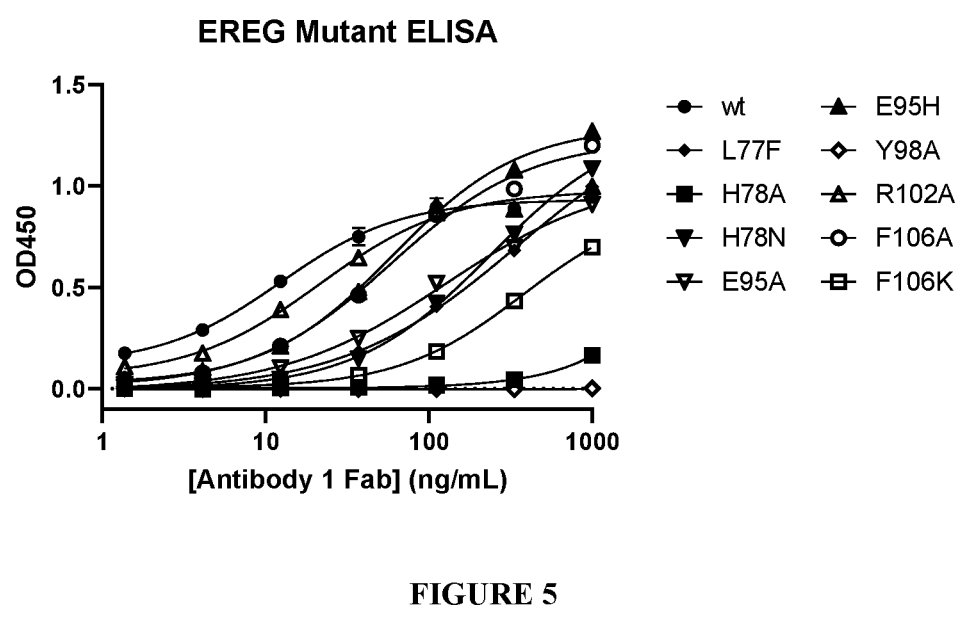

Point mutants were evaluated by ELISA with epiregulin mutants coated on the plate, Antibody 1 Fab dilutions series added, and signal measured by anti-kappa secondary (see FIG. 5). With exception to Y98A, all mutants showed diminished binding. H78A nearly knocked out binding, and Y98A did not exhibit detectable binding at the concentrations tested.

Results in Table 9 show a range of weaker affinities for mutants of 3-fold for R102A up to >1000 fold for F106K at pH 7.4.

Human EGFR Ligand Epitope Alignment

Figure 6:
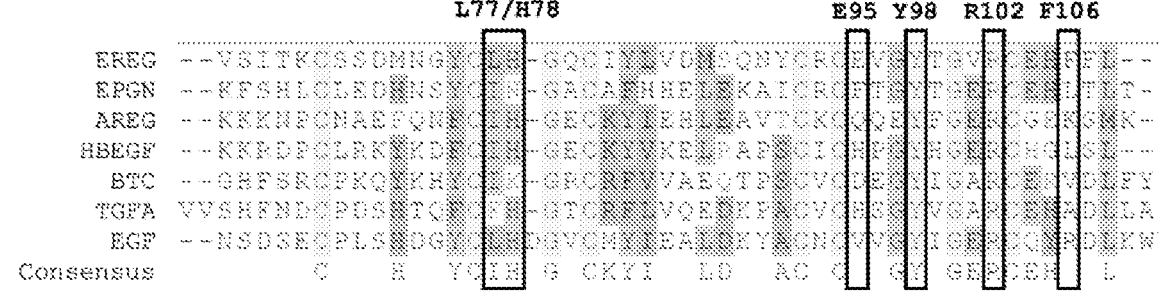
FIG. 6. Human EGFR ligand epitope (EGF-like domains) alignment for Antibody 1. Ligand sequences are provided in the Listing of Amino Acid and Nucleotide Sequences as SEQ ID NO's: 13 and 55-60.

In context of EGFR ligand sequence alignment (FIG. 6), the data show that E95 and F106 are the key epitope positions for EREG selectivity. The 100% conserved Y98 and R102 positions, while important for binding, are not contributing to selectivity. L77 and H78 are also critical for binding and impact selectivity, but they are highly conserved across the EGFR ligands and therefore not as EREG specific. These results demonstrate not only the structural basis for binding and exquisite selectivity of Antibody 1 for EREG, but also inform ligand and species selectivity from the epitope mapping studies.

```
Listing of Amino Acid and Nucleotide Sequences
Heavy Chain of Antibody 1
                                        (SEQ ID NO: 1)
QVQLQESGPGLVKPSETLSLTCTVSGGSISSYYWSWIRQPAGKGLEWIGRI

YPSGNTNYNPSLKSRVTISVDTSKNQFSLKLSSVTAADTAVYYCARGGLVM

DVWGQGTLVTVSSASTKGPSVFPLAPCSRSTSESTAALGCLVKDYFPEPVT

VSWNSGALTSGVHTFPAVLQSSGLYSLSSVVTVPSSSLGTKTYTCNVDHKP

SNTKVDKRVESKYGPPCPPCPAPEAAGGPSVFLFPPKPKDTLMISRTPEVT

CVVVDVSQEDPEVQFNWYVDGVEVHNAKTKPREEQFNSTYRVVSVLTVLHQ

DWLNGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRLTVD

KSRWQEGNVFSCSVMHEALHNHYTQKSLSLSLG

Light Chain of Antibody 1
                                        (SEQ ID NO: 2)
EIVLTQSPGTLSLSPGERATLSCRASQSVEFSYLAWYQQKPGQAPRLLIYG

ASSRATGIPDRFSGSGSGTDFTLTISRLEPEDFAVYYCHQYGTNPFTFGQG

TKVEIKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLSS

PVTKSFNRGEC

HCVR of Antibody 1
                                        (SEQ ID NO: 3)
QVQLQESGPGLVKPSETLSLTCTVSGGSISSYYWSWIRQPAGKGLEWIGRI

YPSGNTNYNPSLKSRVTISVDTSKNQFSLKLSSVTAADTAVYYCARGGLVM

DVWGQGTLVTVSS

LCVR of Antibody 1
                                        (SEQ ID NO: 4)
EIVLTQSPGTLSLSPGERATLSCRASQSVEFSYLAWYQQKPGQAPRLLIYG

ASSRATGIPDRFSGSGSGTDFTLTISRLEPEDFAVYYCHQYGTNPFTFGQG

TKVEIK

HCDRI of Antibody 1
                                        (SEQ ID NO: 5)
TVSGGSISSYYWS HCDR2 of Antibody 1
                                        (SEQ ID NO: 6)
RIYPSGNTN HCDR3 of Antibody 1
                                        (SEQ ID NO: 7)
ARGGLVMDV LCDR1 of Antibody 1
                                        (SEQ ID NO: 8)
RASQSVEFSYLA LCDR2 of Antibody 1
                                        (SEQ ID NO: 9)
YGASSRAT LCDR3 of Antibody 1
                                        (SEQ ID NO: 10)
HQYGTNPFT DNA Encoding the Heavy Chain of Antibody 1
                                        (SEQ ID NO: 11)
CAGGTGCAGCTGCAGGAGTCGGGTCCAGGACTGGTGAAGCCTTCGGAGACC
```

-continued

```
CTGTCCCTCACCTGCACTGTCTCTGGTGGCTCCATCAGTTCGTACTACTGG

AGCTGGATTCGGCAGCCCGCAGGGAAGGGACTGGAGTGGATTGGGAGGATC

TATCCGAGTGGGAACACCAACTACAACCCCTCCCTCAAGAGTCGAGTCACC

ATATCAGTAGACACGTCCAAGAACCAGTTCTCCCTGAAGCTGAGCTCTGTG

ACCGCTGCGGACACGGCCGTGTATTACTGTGCGAGAGGAGGACTGGTGATG

GACGTGTGGGGACAGGGAACACTAGTGACCGTGAGTAGCGCCTCCACCAAG

GGCCCATCGGTCTTCCCGCTAGCGCCCTGCTCCAGGAGCACCTCCGAGAGC

ACAGCCGCCCTGGGCTGCCTGGTCAAGGACTACTTCCCCGAACCGGTGACG

GTGTCGTGGAACTCAGGCGCCCTGACCAGCGGCGTGCACACCTTCCCGGCT

GTCCTACAGTCCTCAGGACTCTACTCCCTCAGCAGCGTGGTGACCGTGCCC

TCCAGCAGCTTGGGCACGAAGACCTACACCTGCAACGTAGATCACAAGCCC

AGCAACACCAAGGTGGACAAGAGAGTTGAGTCCAAATATGGTCCCCCATGC

CCACCCTGCCCAGCACCTGAGGCCGCCGGGGGACCATCAGTCTTCCTGTTC

CCCCCAAAACCCAAGGACACTCTCATGATCTCCCGGACCCCTGAGGTCACG

TGCGTGGTGGTGGACGTGAGCCAGGAAGACCCCGAGGTCCAGTTCAACTGG

TACGTGGATGGCGTGGAGGTGCATAATGCCAAGACAAAGCCGCGGGAGGAG

CAGTTCAACAGCACGTACCGTGTGGTCAGCGTCCTCACCGTCCTGCACCAG

GACTGGCTGAACGGCAAGGAGTACAAGTGCAAGGTCTCCAACAAAGGCCTC

CCGTCCTCCATCGAGAAAACCATCTCCAAAGCCAAAGGGCAGCCCCGAGAG

CCACAGGTGTACACCCTGCCCCCATCCCAGGAGGAGATGACCAAGAACCAG

GTCAGCCTGACCTGCCTGGTCAAAGGCTTCTACCCCAGCGACATCGCCGTG

GAGTGGGAAAGCAATGGGCAGCCGGAGAACAACTACAAGACCACGCCTCCC

GTGCTGGACTCCGACGGCTCCTTCTTCCTCTACAGCAGGCTAACCGTGGAC

AAGAGCAGGTGGCAGGAGGGGAATGTCTTCTCATGCTCCGTGATGCATGAG

GCTCTGCACAACCACTACACACAGAAGAGCCTCTCCCTGTCTCTGGGT

DNA Encoding the Light Chain of Antibody 1
                                        (SEQ ID NO: 12)
GAAATTGTGTTGACGCAGTCTCCAGGCACCCTGTCTTTGTCTCCAGGGGAA

AGAGCCACCCTCTCCTGCAGGGCCAGTCAGTCTGTGGAATTCAGCTACTTA

GCCTATGGTGCATCCAGCAGGGCCACTTGGTACCAGCAGAAACCTGGCCAG

GCTCCCAGGCTCCTCATCTATGGTGCATCCAGCAGGGCCACTGGCATCCCA

GACAGGTTCAGTGGCAGTGGGTCTGGGACAGACTTCACTCTCACCATCAGC

AGACTGGAGCCTGAAGATTTTGCAGTGTATTACTGTCACCAGTACGGAACA

AACCCGTTCACATTCGGGCAGGGAACCAAGGTTGAAATAAAGCGAACTGTG

GCTGCACCATCTGTCTTCATCTTCCCGCCATCTGATGAGCAGTTGAAATCT

GGAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGAG

AGTGTCACAGAGCAGGACAGCAAGGACAGCACCTACAGCCTCAGCAGCACC

CTGACGCTGAGCAAAGCAGACTACGAGAAACACAAAGTCTACGCCTGCGAA

GTCACCCATCAGGGCCTGAGCTCGCCCGTCACAAAGAGCTTCAACAGGGGA

GAGTGC
```

-continued

Human epiregulin
(SEQ ID NO: 13)
VSITKCSSDMNGYCLHGQCIYLVDMSQNYCRCEVGYTGVRCEHFFL

Human epiregulin construct
(SEQ ID NO: 14)
GPGVSITKCSSDMNGYCLHGQCIYLVDMSQNYCRCEVGYTGVRCEHFFLG Cynomolgus monkey epiregulin
(SEQ ID NO: 15)
VSITKCNSDMNGYCLHGQCIYLVDMSQNYCRCEVGYTGVRCEHFYL Rat epiregulin
(SEQ ID NO: 16)
VLITKCSSDMDGYCLHGHCIYLVDMSEKYCRCEVGYTGLRCEHFFL Rabbit epiregulin
(SEQ ID NO: 17)
VSITKCSSDMNGYCLHGQCIYLVDMSENYCRCEVGYTGVRCEHFFL Full length human epiregulin (membrane bound, with
T111P mutation)
(SEQ ID NO: 18)
MTAGRRMEMLCAGRVPALLLCLGFHLLQAVLSTTVIPSCIPGESSDNCTAL

VQTEDNPRVAQVSITKCSSDMNGYCLHGQCIYLVDMSQNYCRCEVGYTGVR

CEHFFLTVPQPLSKEYVALTVILIILFLITVVGSTYYFCRWYRNRKSKEPK

KEYERVTSGDPELPQV

Monomeric Ec human epiregulin
(SEQ ID NO: 19)
APEAAGGPSVFLFPPPKPKDTLMISRTPEVTCVVVDVSQEDPEVQFNWYVDG

VEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWES

NGQPENNYKTTPPVLDSDGSFQLESRLTVDKSRWQEGNVFSCSVMHEALHN

HYTQKSLSLSLGGGGGSGGGGSLEVLFQGPGVSITKCSSDMNGYCLHGQCI

YLVDMSQNYCRCEVGYTGVRCEHFFLG

Cleaved mouse EREG
(SEQ ID NO: 20)
GPGVQITKCSSDMDGYCLHGQCIYLVDMREKFCRCEVGYTGLRCEHFFLG Mouse TGFa His
(SEQ ID NO: 21)
VVSHFNKCPDSHTQYCFHGTCRFLVQEEKPACVCHSGYVGVRCEHADLLAG

HHHHHH

HCDR1 of Antibody 1 (Kabat)
(SEQ ID NO: 22)
SYYWS

HCDR2 of Antibody 1 (Kabat)
(SEQ ID NO: 23)
RIYPSGNTNYNPSLKS

HCDR3 of Antibody 1 (Kabat)
(SEQ ID NO: 24)
GGLVMDV

LCDR1 of Antibody 1 (Kabat)
(SEQ ID NO: 25)
RASQSVEFSYLA

LCDR2 of Antibody 1 (Kabat)
(SEQ ID NO: 26)
GASSRAT

LCDR3 of Antibody 1 (Kabat)
(SEQ ID NO: 27)
HQYGTNPFT

HCDR1 of Antibody 1 (Chothia)
(SEQ ID NO: 28)

-continued

GGSISSY

HCDR2 of Antibody 1 (Chothia)
(SEQ ID NO: 29)
YPSGN

HCDR3 of Antibody 1 (Chothia)
(SEQ ID NO: 30)
GGLVMDV

LCDR1 of Antibody 1 (Chothia)
(SEQ ID NO: 31)
RASQSVEFSYLA

LCDR2 of Antibody 1 (Chothia)
(SEQ ID NO: 32)
GASSRAT

LCDR3 of Antibody 1 (Chothia)
(SEQ ID NO: 33)
HQYGTNPFT

HCDRI of Antibody 1 (IMGT)
(SEQ ID NO: 34)
GGSISSYY

HCDR2 of Antibody 1 (IMGT)
(SEQ ID NO: 35)
IYPSGNT

HCDR3 of Antibody 1 (IMGT)
(SEQ ID NO: 36)
ARGGLVMDV

LCDRI of Antibody 1 (IMGT)
(SEQ ID NO: 37)
QSVEFSY

LCDR2 of Antibody 1 (IMGT)
(SEQ ID NO: 38)
GAS

LCDR3 of Antibody 1 (IMGT)
(SEQ ID NO: 39)
HQYGTNPFT

IgG4PAA hinge region
(SEQ ID NO: 40)
ESKYGPPCPPCP

IgG4PAA Fc region
(SEQ ID NO: 41)
APEAAGGPSVFLFPPPKPKDTLMISRTPEVTCVVVDVSQEDPEVQFNWYVDG

VEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHEALHN

HYTQKSLSLSLG

Mono Fc huEREG L77F
(SEQ ID NO: 42)
APEAAGGPSVFLFPPPKPKDTLMISRTPEVTCVVVDVSQEDPEVQFNWYVDG

VEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWES

NGQPENNYKTTPPVLDSDGSFQLESRLTVDKSRWQEGNVFSCSVMHEALHN

HYTQKSLSLSLGGGGGSGGGGSLEVLFQGPGVSITKCSSDMNGYCFHGQCI

YLVDMSQNYCRCEVGYTGVRCEHFFLG

Mono Fc huEREG H78A
(SEQ ID NO: 43)
APEAAGGPSVFLFPPPKPKDTLMISRTPEVTCVVVDVSQEDPEVQFNWYVDG

VEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWES

NGQPENNYKTTPPVLDSDGSFQLESRLTVDKSRWQEGNVFSCSVMHEALHN

HYTQKSLSLSLGGGGGSGGGGSLEVLFQGPGVSITKCSSDMNGYCLAGQCI

YLVDMSQNYCRCEVGYTGVRCEHFFLG

Mono Fc huEREG H78N
(SEQ ID NO: 44)
APEAAGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWES

NGQPENNYKTTPPVLDSDGSFQLESRLTVDKSRWQEGNVFSCSVMHEALHN

HYTQKSLSLSLGGGGGSGGGGSLEVLFQGPGVSITKCSSDMNGYCLNGQCI

YLVDMSQNYCRCEVGYTGVRCEHFFLG

Mono Fc huEREG E95A
(SEQ ID NO: 45)
APEAAGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWES

NGQPENNYKTTPPVLDSDGSFQLESRLTVDKSRWQEGNVFSCSVMHEALHN

HYTQKSLSLSLGGGGGSGGGGSLEVLFQGPGVSITKCSSDMNGYCLHGQCI

YLVDMSQNYCRCAVGYTGVRCEHFFLG

Mono Fc huEREG E95H
(SEQ ID NO: 46)
APEAAGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWES

NGQPENNYKTTPPVLDSDGSFQLESRLTVDKSRWQEGNVFSCSVMHEALHN

HYTQKSLSLSLGGGGGSGGGGSLEVLFQGPGVSITKCSSDMNGYCLHGQCI

YLVDMSQNYCRCHVGYTGVRCEHFFLG

Mono Fc huEREG Y98A
(SEQ ID NO: 47)
APEAAGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWES

NGQPENNYKTTPPVLDSDGSFQLESRLTVDKSRWQEGNVFSCSVMHEALHN

HYTQKSLSLSLGGGGGSGGGGSLEVLFQGPGVSITKCSSDMNGYCLHGQCI

YLVDMSQNYCRCEVGATGVRCEHFFLG

Mono Fc huEREG R102A
(SEQ ID NO: 48)
APEAAGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWES

NGQPENNYKTTPPVLDSDGSFQLESRLTVDKSRWQEGNVFSCSVMHEALHN

HYTQKSLSLSLGGGGGSGGGGSLEVLFQGPGVSITKCSSDMNGYCLHGQCI

YLVDMSQNYCRCEVGYTGVACEHFFLG

Mono Fc huEREG F106A
(SEQ ID NO: 49)
APEAAGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWES

NGQPENNYKTTPPVLDSDGSFQLESRLTVDKSRWQEGNVFSCSVMHEALHN

HYTQKSLSLSLGGGGGSGGGGSLEVLFQGPGVSITKCSSDMNGYCLHGQCI

YLVDMSQNYCRCEVGYTGVRCEHAFLG

Mono Fc huEREG F106K
(SEQ ID NO: 50)
APEAAGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWES

NGQPENNYKTTPPVLDSDGSFQLESRLTVDKSRWQEGNVFSCSVMHEALHN

HYTQKSLSLSLGGGGGSGGGGSLEVLFQGPGVSITKCSSDMNGYCLHGQCI

YLVDMSQNYCRCEVGYTGVRCEHAKLG

Antibody 1 Fab HC
(SEQ ID NO: 51)
QVQLQESGPGLVKPSETLSLTCTVSGGSISSYYWSWIRQPAGKGLEWIGRI

YPSGNTNYNPSLKSRVTISVDTSKNQFSLKLSSVTAADTAVYYCARGGLVM

DVWGQGTLVTVSSASTKGPSVFPLAPCSRSTSESTAALGCLVKDYFPEPVT

VSWNSGALTSGVHTFPAVLQSSGLYSLSSVVTVPSSSLGTKTYTCNVDHKP

SNTKVDKRVESK

Antibody 1 Fab LC
(SEQ ID NO: 52)
EIVLTQSPGTLSLSPGERATLSCRASQSVEFSYLAWYQQKPGQAPRLLIYG

ASSRATGIPDRFSGSGSGTDFTLTISRLEPEDFAVYYCHQYGTNPFTFGQG

TKVEIKRTVAAPSVFIFPPSDEQLKSGTASVVCLLNNFYPREAKVQWKVDN

ALQSGNSQESVTEQDSKDSTYSLSSTLTLSKADYEKHKVYACEVTQGTTSV

TKSFNRGEC

Antibody 1 VR chimera h/mIgG1 HC
(SEQ ID NO: 53)
QVQLQESGPGLVKPSETLSLTCTVSGGSISSYYWSWIRQPAGKGLEWIGRI

YPSGNTNYNPSLKSRVTISVDTSKNQFSLKLSSVTAADTAVYYCARGGLVM

DVWGQGTLVTVSSASTKGPSVFPLAPGSAAQTNSMVTLGCLVKGYFPEPVT

VTWNSGSLSSGVHTFPAVLQSDLYTLSSSVTVPSSTWPSETVTCNVAHPAS

STKVDKKIVPRDCGCKPCICTVPEVSSVFIFPPKPKDVLTITLTPKVTCVV

VDISKDDPEVQFSWFVDDVEVHTAQTQPREEQFNSTFRSVSELPIMHQDWL

NGKEFKCRVNSAAFPAPIEKTISKTKGRPKAPQVYTIPPPKEQMAKDKVSL

TCMITDFFPEDITVEWQWNGQPAENYKNTQPIMDTDGSYFVYSKLNVQKSN

WEAGNTFTCSVLHEGLHNHHTEKSLSHSPGK

Antibody 1 VR chimera h/mKappa LC
(SEQ ID NO: 54)
EIVLTQSPGTLSLSPGERATLSCRASQSVEFSYLAWYQQKPGQAPRLLIYG

ASSRATGIPDRFSGSGSGTDFTLTISRLEPEDFAVYYCHQYGTNPFTFGQG

TKVEIKRTVAAPTVSIFPPSSEQLTSGGASVVCFLNNFYPKDINVKWKIDG

-continued

SERQNGVLNSWTDQDSKDSTYSMSSTLTLTKDEYERHNSYTCEATHKTSTS

PIVKSFNRNEC human epigen/EPGN
                                    (SEQ ID NO: 55)
KFSHLCLEDHNSYCINGACAFHHELEKAICRCFTGYTGERCEHLTLT human amphiregulin/AREG
                                    (SEQ ID NO: 56)
KKKNPCNAEFQNFCIHGECKYIEHLEAVTCKCQQEYFGERCGEKSMK human heparin binding epidermal growth factor/HBEGF
                                    (SEQ ID NO: 57)

-continued

KKRDPCLRKYKDFCIHGECKYVKELRAPSCICHPGYHGERCHGLSL human betacellulin/BTC
                                    (SEQ ID NO: 58)
GHFSRCPKQYKHYCIKGRCRFVVAEQTPSCVCDEGYIGARCERVDLFY human transforming growth factor alpha/TGFa
                                    (SEQ ID NO: 59)
WSHFNDCPDSHTQFCFHGTCRFLVQEDKPACVCHSGYVGARCEHADLLA human epidermal growth factor/EGF
                                    (SEQ ID NO: 60)
NSDSECPLSHDGYCLHDGVCMYIEALDKYACNCVVGYIGERCQYRDLKW

We claim:

1. An antibody that binds human epiregulin wherein the antibody comprises a heavy chain variable region (VH) and a light chain variable region (VL), wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises SEQ ID NO: 5,
the HCDR2 comprises SEQ ID NO: 6,
the HCDR3 comprises SEQ ID NO: 7,
the LCDR1 comprises SEQ ID NO: 8,
the LCDR2 comprises SEQ ID NO: 9, and
the LCDR3 comprises SEQ ID NO: 10.

2. The antibody of claim 1, wherein the VH comprises SEQ ID NO: 3 and the VL comprises SEQ ID NO: 4.

3. The antibody of claim 1, wherein the antibody comprises a heavy chain (HC) comprising SEQ ID NO: 1 and a light chain (LC) comprising SEQ ID NO: 2.

4. A pharmaceutical composition comprising the antibody of any one of claims 1-3, and a pharmaceutically acceptable excipient, diluent or carrier.

* * * * *

SEQUENCE LISTING

<160> NUMBER OF SEQ ID NOS: 60

<210> SEQ ID NO 1
<211> LENGTH: 441
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Pro Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Leu Val Met Asp Val Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
            195                 200                 205

Val Asp Lys Arg Val Glu Ser Lys Tyr Gly Pro Pro Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp

-continued

```
                 260                 265                 270

Tyr Val Asp Gly Val Glu Val His Asn Ala Lys Thr Lys Pro Arg Glu
            275                 280                 285

Glu Gln Phe Asn Ser Thr Tyr Arg Val Val Ser Val Leu Thr Val Leu
        290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
        370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
        435                 440

<210> SEQ ID NO 2
<211> LENGTH: 215
<212> TYPE: PRT
<213> ORGANISM: Artificial Sequence
<220> FEATURE:
<223> OTHER INFORMATION: Synthetic Construct

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Glu Phe Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr Gly Thr Asn Pro
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
```

-continued

```
                    180                185                190

Tyr Ala Cys Glu Val Thr His Gln Gly Leu Ser Ser Pro Val Thr Lys
            195                200                205

Ser Phe Asn Arg Gly Glu Cys
        210                215

<210> SEQ ID NO 3
<211> LENGTH: 115
<212> TYPE: PRT
<213> ORGANISM: Artificial Sequence
<220> FEATURE:
<223> OTHER INFORMATION: Synthetic Construct

<400> SEQUENCE: 3

Gln Val Gln Leu Gln Glu Ser Gly Pro Gly Leu Val Lys Pro Ser Glu
1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Pro Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Leu Val Met Asp Val Trp Gly Gln Gly Thr Leu Val Thr
            100                105                110

Val Ser Ser
        115

<210> SEQ ID NO 4
<211> LENGTH: 108
<212> TYPE: PRT
<213> ORGANISM: Artificial Sequence
<220> FEATURE:
<223> OTHER INFORMATION: Synthetic Construct

<400> SEQUENCE: 4

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Glu Phe Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr Gly Thr Asn Pro
                85                  90                  95

Phe Thr Phe Gly Gln Gly Thr Lys Val Glu Ile Lys
            100                105

<210> SEQ ID NO 5
<211> LENGTH: 13
<212> TYPE: PRT
<213> ORGANISM: Artificial Sequence
<220> FEATURE:
```

<223> OTHER INFORMATION: Synthetic Construct

<400> SEQUENCE: 5

Thr Val Ser Gly Gly Ser Ile Ser Ser Tyr Tyr Trp Ser
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Arg Ile Tyr Pro Ser Gly Asn Thr Asn
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Ala Arg Gly Gly Leu Val Met Asp Val
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic Construct

<400> SEQUENCE: 8

Arg Ala Ser Gln Ser Val Glu Phe Ser Tyr Leu Ala
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Tyr Gly Ala Ser Ser Arg Ala Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

His Gln Tyr Gly Thr Asn Pro Phe Thr
1               5

<210> SEQ ID NO 11
<211> LENGTH: 1323
<212> TYPE: DNA
<213> ORGANISM: Artificial Sequence
<220> FEATURE:
<223> OTHER INFORMATION: Synthetic Construct -continued

<400> SEQUENCE: 11

```
caggtgcagc tgcaggagtc gggtccagga ctggtgaagc cttcggagac cctgtccctc      60
acctgcactg tctctggtgg ctccatcagt tcgtactact ggagctggat tcggcagccc     120
gcagggaagg gactggagtg gattgggagg atctatccga gtgggaacac caactacaac     180
ccctccctca agagtcgagt caccatatca gtagacacgt ccaagaacca gttctccctg     240
aagctgagct ctgtgaccgc tgcggacacg gccgtgtatt actgtgcgag aggaggactg     300
gtgatggacg tgtggggaca gggaacacta gtgaccgtga gtagcgcctc caccaagggc     360
ccatcggtct tccccgctagc gccctgctcc aggagcacct ccgagagcac agccgccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcacga gacctacac ctgcaacgta     600 gatcacaagc ccagcaacac caaggtggac aagagagttg agtccaaata tggtcccca     660 tgcccaccct gcccagcacc tgaggccgcc ggggggaccat cagtcttcct gttcccccca     720
aaacccaagg acactctcat gatctcccgg acccctgagg tcacgtgcgt ggtggtggac     780
gtgagccagg aagaccccga ggtccagttc aactggtacg tggatggcgt ggaggtgcat     840
aatgccaaga caaagccgcg ggaggagcag ttcaacagca cgtaccgtgt ggtcagcgtc     900
ctcaccgtcc tgcaccagga ctggctgaac ggcaaggagt acaagtgcaa ggtctccaac     960
aaaggcctcc cgtcctccat cgagaaaacc atctccaaag ccaaagggca gccccgagag    1020
ccacaggtgt acaccctgcc cccatcccag gaggagatga ccaagaacca ggtcagcctg    1080
acctgcctgg tcaaaggctt ctaccccagc gacatcgccg tggagtggga aagcaatggg    1140
cagccggaga acaactacaa gaccacgcct cccgtgctgg actccgacgg ctccttcttc    1200
ctctacagca ggctaaccgt ggacaagagc aggtggcagg aggggaatgt cttctcatgc    1260
tccgtgatgc atgaggctct gcacaaccac tacacacaga gagcctctc cctgtctctg    1320 ggt                                                                 1323
```

```
<210> SEQ ID NO 12
<211> LENGTH: 669
<212> TYPE: DNA
<213> ORGANISM: Artificial Sequence
<220> FEATURE:
<223> OTHER INFORMATION: Synthetic Construct
```

<400> SEQUENCE: 12

```
gaaattgtgt tgacgcagtc tccaggcacc ctgtctttgt ctccagggga aagagccacc      60
ctctcctgca gggccagtca gtctgtggaa ttcagctact tagcctatgg tgcatccagc     120
agggccactt ggtaccagca gaaacctggc caggctccca ggctcctcat ctatggtgca     180
tccagcaggg ccactggcat cccagacagg ttcagtggca gtgggtctgg gacagacttc     240
actctcacca tcagcagact ggagcctgaa gattttgcag tgtattactg tcaccagtac     300
ggaacaaacc cgttcacatt cgggcaggga accaaggttg aaataaagcg aactgtggct     360
gcaccatctg tcttcatctt cccgccatct gatgagcagt tgaaatctgg aactgcctct     420
gttgtgtgcc tgctgaataa cttctatccc agagaggcca agtacagtg gaaggtggat     480 aacgccctcc aatcgggtaa ctcccaggag agtgtcacag agcaggacag caaggacagc     540
acctacagcc tcagcagcac cctgacgctg agcaaagcag actacgagaa acacaaagtc     600
```

```
tacgcctgcg aagtcaccca tcagggcctg agctcgcccg tcacaaagag cttcaacagg       660
ggagagtgc                                                               669
```

```
<210> SEQ ID NO 13
<211> LENGTH: 46
<212> TYPE: PRT
<213> ORGANISM: Homo sapiens

<400> SEQUENCE: 13

Val Ser Ile Thr Lys Cys Ser Ser Asp Met Asn Gly Tyr Cys Leu His
1               5                   10                  15

Gly Gln Cys Ile Tyr Leu Val Asp Met Ser Gln Asn Tyr Cys Arg Cys
            20                  25                  30

Glu Val Gly Tyr Thr Gly Val Arg Cys Glu His Phe Phe Leu
        35                  40                  45
```

```
<210> SEQ ID NO 14
<211> LENGTH: 50
<212> TYPE: PRT
<213> ORGANISM: Homo sapiens

<400> SEQUENCE: 14

Gly Pro Gly Val Ser Ile Thr Lys Cys Ser Ser Asp Met Asn Gly Tyr
1               5                   10                  15

Cys Leu His Gly Gln Cys Ile Tyr Leu Val Asp Met Ser Gln Asn Tyr
            20                  25                  30

Cys Arg Cys Glu Val Gly Tyr Thr Gly Val Arg Cys Glu His Phe Phe
        35                  40                  45

Leu Gly
    50
```

```
<210> SEQ ID NO 15
<211> LENGTH: 46
<212> TYPE: PRT
<213> ORGANISM: Macaca fascicularis

<400> SEQUENCE: 15

Val Ser Ile Thr Lys Cys Asn Ser Asp Met Asn Gly Tyr Cys Leu His
1               5                   10                  15

Gly Gln Cys Ile Tyr Leu Val Asp Met Ser Gln Asn Tyr Cys Arg Cys
            20                  25                  30

Glu Val Gly Tyr Thr Gly Val Arg Cys Glu His Phe Tyr Leu
        35                  40                  45
```

```
<210> SEQ ID NO 16
<211> LENGTH: 46
<212> TYPE: PRT
<213> ORGANISM: Rattus norvegicus

<400> SEQUENCE: 16

Val Leu Ile Thr Lys Cys Ser Ser Asp Met Asp Gly Tyr Cys Leu His
1               5                   10                  15

Gly His Cys Ile Tyr Leu Val Asp Met Ser Glu Lys Tyr Cys Arg Cys
            20                  25                  30

Glu Val Gly Tyr Thr Gly Leu Arg Cys Glu His Phe Phe Leu
        35                  40                  45
```

```
<210> SEQ ID NO 17
<211> LENGTH: 46
<212> TYPE: PRT
```

<213> ORGANISM: Oryctolagus cuniculus

<400> SEQUENCE: 17

Val Ser Ile Thr Lys Cys Gly Ser Asp Met Asn Gly Tyr Cys Leu His
1               5                   10                  15

Gly Gln Cys Ile Tyr Leu Val Asp Met Ser Glu Asn Tyr Cys Arg Cys
            20                  25                  30

Glu Val Gly Tyr Thr Gly Val Arg Cys Glu His Phe Phe Leu
        35                  40                  45

<210> SEQ ID NO 18
<211> LENGTH: 169
<212> TYPE: PRT
<213> ORGANISM: Artificial Sequence
<220> FEATURE:
<223> OTHER INFORMATION: Synthetic Construct

<400> SEQUENCE: 18

Met Thr Ala Gly Arg Arg Met Glu Met Leu Cys Ala Gly Arg Val Pro
1               5                   10                  15

Ala Leu Leu Leu Cys Leu Gly Phe His Leu Leu Gln Ala Val Leu Ser
            20                  25                  30

Thr Thr Val Ile Pro Ser Cys Ile Pro Gly Glu Ser Ser Asp Asn Cys
            35                  40                  45

Thr Ala Leu Val Gln Thr Glu Asp Asn Pro Arg Val Ala Gln Val Ser
        50                  55                  60

Ile Thr Lys Cys Ser Ser Asp Met Asn Gly Tyr Cys Leu His Gly Gln
65                  70                  75                  80

Cys Ile Tyr Leu Val Asp Met Ser Gln Asn Tyr Cys Arg Cys Glu Val
            85                  90                  95

Gly Tyr Thr Gly Val Arg Cys Glu His Phe Phe Leu Thr Val Pro Gln
            100                 105                 110

Pro Leu Ser Lys Glu Tyr Val Ala Leu Thr Val Ile Leu Ile Ile Leu
        115                 120                 125

Phe Leu Ile Thr Val Val Gly Ser Thr Tyr Tyr Phe Cys Arg Trp Tyr
    130                 135                 140

Arg Asn Arg Lys Ser Lys Glu Pro Lys Lys Glu Tyr Glu Arg Val Thr
145                 150                 155                 160

Ser Gly Asp Pro Glu Leu Pro Gln Val
                165

<210> SEQ ID NO 19
<211> LENGTH: 282
<212> TYPE: PRT
<213> ORGANISM: Artificial Sequence
<220> FEATURE:
<223> OTHER INFORMATION: Synthetic Construct

<400> SEQUENCE: 19

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His

```
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
                100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Gln Leu
                165                 170                 175

Glu Ser Arg Leu Thr Val Asp Lys Ser Arg Trp Gln Glu Gly Asn Val
                180                 185                 190

Phe Ser Cys Ser Val Met His Glu Ala Leu His Asn His Tyr Thr Gln
                195                 200                 205

Lys Ser Leu Ser Leu Ser Leu Gly Gly Gly Gly Ser Gly Gly Gly
        210                 215                 220

Gly Ser Leu Glu Val Leu Phe Gln Gly Pro Gly Val Ser Ile Thr Lys
225                 230                 235                 240

Cys Ser Ser Asp Met Asn Gly Tyr Cys Leu His Gly Gln Cys Ile Tyr
                245                 250                 255

Leu Val Asp Met Ser Gln Asn Tyr Cys Arg Cys Glu Val Gly Tyr Thr
                260                 265                 270

Gly Val Arg Cys Glu His Phe Phe Leu Gly
                275                 280

<210> SEQ ID NO 20
<211> LENGTH: 50
<212> TYPE: PRT
<213> ORGANISM: Mus musculus

<400> SEQUENCE: 20

Gly Pro Gly Val Gln Ile Thr Lys Cys Ser Ser Asp Met Asp Gly Tyr
1               5                   10                  15

Cys Leu His Gly Gln Cys Ile Tyr Leu Val Asp Met Arg Glu Lys Phe
                20                  25                  30

Cys Arg Cys Glu Val Gly Tyr Thr Gly Leu Arg Cys Glu His Phe Phe
        35                  40                  45

Leu Gly
    50

<210> SEQ ID NO 21
<211> LENGTH: 57
<212> TYPE: PRT
<213> ORGANISM: Artificial Sequence
<220> FEATURE:
<223> OTHER INFORMATION: Synthetic Construct

<400> SEQUENCE: 21

Val Val Ser His Phe Asn Lys Cys Pro Asp Ser His Thr Gln Tyr Cys
1               5                   10                  15

Phe His Gly Thr Cys Arg Phe Leu Val Gln Glu Glu Lys Pro Ala Cys
                20                  25                  30

Val Cys His Ser Gly Tyr Val Gly Val Arg Cys Glu His Ala Asp Leu
        35                  40                  45
```

```
Leu Ala Gly His His His His His His
    50                  55

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct

<400> SEQUENCE: 22

Ser Tyr Tyr Trp Ser
1               5

<210> SEQ ID NO 23
<211> LENGTH: 16
<212> TYPE: PRT
<213> ORGANISM: Artificial Sequence
<220> FEATURE:
<223> OTHER INFORMATION: Synthetic Construct

<400> SEQUENCE: 23

Arg Ile Tyr Pro Ser Gly Asn Thr Asn Tyr Asn Pro Ser Leu Lys Ser
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct

<400> SEQUENCE: 24

Gly Gly Leu Val Met Asp Val
1               5

<210> SEQ ID NO 25
<211> LENGTH: 12
<212> TYPE: PRT
<213> ORGANISM: Artificial Sequence
<220> FEATURE:
<223> OTHER INFORMATION: Synthetic Construct

<400> SEQUENCE: 25

Arg Ala Ser Gln Ser Val Glu Phe Ser Tyr Leu Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Synthetic Construct

<400> SEQUENCE: 26

Gly Ala Ser Ser Arg Ala Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27
```

-continued

```
His Gln Tyr Gly Thr Asn Pro Phe Thr
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Construct

<400> SEQUENCE: 28

Gly Gly Ser Ile Ser Ser Tyr
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Tyr Pro Ser Gly Asn
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Gly Gly Leu Val Met Asp Val
1               5

<210> SEQ ID NO 31
<211> LENGTH: 12
<212> TYPE: PRT
<213> ORGANISM: Artificial Sequence
<220> FEATURE:
<223> OTHER INFORMATION: Synthetic Construct

<400> SEQUENCE: 31

Arg Ala Ser Gln Ser Val Glu Phe Ser Tyr Leu Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Synthetic Construct

<400> SEQUENCE: 32

Gly Ala Ser Ser Arg Ala Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

His Gln Tyr Gly Thr Asn Pro Phe Thr
```

```
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

Gly Gly Ser Ile Ser Ser Tyr Tyr
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct

<400> SEQUENCE: 35

Ile Tyr Pro Ser Gly Asn Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct

<400> SEQUENCE: 36

Ala Arg Gly Gly Leu Val Met Asp Val
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Gln Ser Val Glu Phe Ser Tyr
1               5

<210> SEQ ID NO 38
<211> LENGTH: 3
<212> TYPE: PRT
<213> ORGANISM: Artificial Sequence
<220> FEATURE:
<223> OTHER INFORMATION: Synthetic Construct

<400> SEQUENCE: 38

Gly Ala Ser
1

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct

<400> SEQUENCE: 39

His Gln Tyr Gly Thr Asn Pro Phe Thr
1               5
```

```
<210> SEQ ID NO 40
<211> LENGTH: 12
<212> TYPE: PRT
<213> ORGANISM: Artificial Sequence
<220> FEATURE:
<223> OTHER INFORMATION: Synthetic Construct

<400> SEQUENCE: 40

Glu Ser Lys Tyr Gly Pro Pro Cys Pro Pro Cys Pro
1               5                   10

<210> SEQ ID NO 41
<211> LENGTH: 216
<212> TYPE: PRT
<213> ORGANISM: Artificial Sequence
<220> FEATURE:
<223> OTHER INFORMATION: Synthetic Construct

<400> SEQUENCE: 41

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly
    210                 215

<210> SEQ ID NO 42
<211> LENGTH: 282
<212> TYPE: PRT
<213> ORGANISM: Artificial Sequence
<220> FEATURE:
<223> OTHER INFORMATION: Synthetic construct

<400> SEQUENCE: 42

Ala Pro Glu Ala Ala Gly Gly Pro Ser Val Phe Leu Phe Pro Pro Lys
1               5                   10                  15
```

```
Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Gln Leu
                165                 170                 175

Glu Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Gly Gly Gly Ser Gly Gly Gly
            210                 215                 220

Gly Ser Leu Glu Val Leu Phe Gln Gly Pro Gly Val Ser Ile Thr Lys
225                 230                 235                 240

Cys Ser Ser Asp Met Asn Gly Tyr Cys Phe His Gly Gln Cys Ile Tyr
                245                 250                 255

Leu Val Asp Met Ser Gln Asn Tyr Cys Arg Cys Glu Val Gly Tyr Thr
                260                 265                 270

Gly Val Arg Cys Glu His Phe Phe Leu Gly
            275                 280

<210> SEQ ID NO 43
<211> LENGTH: 282
<212> TYPE: PRT
<213> ORGANISM: Artificial Sequence
<220> FEATURE:
<223> OTHER INFORMATION: Synthetic construct

<400> SEQUENCE: 43

Ala Pro Glu Ala Ala Gly Gly Pro Ser Val Phe Leu Phe Pro Pro Lys
1                   5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

-continued

```
Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Gln Leu
                165                 170                 175

Glu Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Gly Gly Gly Ser Gly Gly Gly
    210                 215                 220

Gly Ser Leu Glu Val Leu Phe Gln Gly Pro Gly Val Ser Ile Thr Lys
225                 230                 235                 240

Cys Ser Ser Asp Met Asn Gly Tyr Cys Leu Ala Gly Gln Cys Ile Tyr
                245                 250                 255

Leu Val Asp Met Ser Gln Asn Tyr Cys Arg Cys Glu Val Gly Tyr Thr
                260                 265                 270

Gly Val Arg Cys Glu His Phe Phe Leu Gly
            275                 280
```

```
<210> SEQ ID NO 44
<211> LENGTH: 282
<212> TYPE: PRT
<213> ORGANISM: Artificial Sequence
<220> FEATURE:
<223> OTHER INFORMATION: Synthetic construct

<400> SEQUENCE: 44
```

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Gln Leu
                165                 170                 175
```

```
Glu Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Gly Gly Gly Gly Ser Gly Gly Gly
            210                 215                 220

Gly Ser Leu Glu Val Leu Phe Gln Gly Pro Gly Val Ser Ile Thr Lys
225                 230                 235                 240

Cys Ser Ser Asp Met Asn Gly Tyr Cys Leu Asn Gly Gln Cys Ile Tyr
                245                 250                 255

Leu Val Asp Met Ser Gln Asn Tyr Cys Arg Cys Glu Val Gly Tyr Thr
                260                 265                 270

Gly Val Arg Cys Glu His Phe Phe Leu Gly
            275                 280

<210> SEQ ID NO 45
<211> LENGTH: 282
<212> TYPE: PRT
<213> ORGANISM: Artificial Sequence
<220> FEATURE:
<223> OTHER INFORMATION: Synthetic construct

<400> SEQUENCE: 45

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
            50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Gln Leu
                165                 170                 175

Glu Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Gly Gly Gly Gly Ser Gly Gly Gly
            210                 215                 220

Gly Ser Leu Glu Val Leu Phe Gln Gly Pro Gly Val Ser Ile Thr Lys
225                 230                 235                 240

Cys Ser Ser Asp Met Asn Gly Tyr Cys Leu His Gly Gln Cys Ile Tyr
                245                 250                 255
```

-continued

```
Leu Val Asp Met Ser Gln Asn Tyr Cys Arg Cys Ala Val Gly Tyr Thr
            260                 265                 270

Gly Val Arg Cys Glu His Phe Phe Leu Gly
        275                 280

<210> SEQ ID NO 46
<211> LENGTH: 282
<212> TYPE: PRT
<213> ORGANISM: Artificial Sequence
<220> FEATURE:
<223> OTHER INFORMATION: Synthetic construct

<400> SEQUENCE: 46

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Gln Leu
                165                 170                 175

Glu Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Gly Gly Gly Ser Gly Gly Gly
        210                 215                 220

Gly Ser Leu Glu Val Leu Phe Gln Gly Pro Gly Val Ser Ile Thr Lys
225                 230                 235                 240

Cys Ser Ser Asp Met Asn Gly Tyr Cys Leu His Gly Gln Cys Ile Tyr
                245                 250                 255

Leu Val Asp Met Ser Gln Asn Tyr Cys Arg Cys His Val Gly Tyr Thr
            260                 265                 270

Gly Val Arg Cys Glu His Phe Phe Leu Gly
        275                 280

<210> SEQ ID NO 47
<211> LENGTH: 282
<212> TYPE: PRT
<213> ORGANISM: Artificial Sequence
<220> FEATURE:
<223> OTHER INFORMATION: Synthetic construct

<400> SEQUENCE: 47
```

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Gln Leu
                165                 170                 175

Glu Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Gly Gly Gly Gly Ser Gly Gly Gly
        210                 215                 220

Gly Ser Leu Glu Val Leu Phe Gln Gly Pro Gly Val Ser Ile Thr Lys
225                 230                 235                 240

Cys Ser Ser Asp Met Asn Gly Tyr Cys Leu His Gly Gln Cys Ile Tyr
                245                 250                 255

Leu Val Asp Met Ser Gln Asn Tyr Cys Arg Cys Glu Val Gly Ala Thr
                260                 265                 270

Gly Val Arg Cys Glu His Phe Phe Leu Gly
        275                 280

<210> SEQ ID NO 48
<211> LENGTH: 282
<212> TYPE: PRT
<213> ORGANISM: Artificial Sequence
<220> FEATURE:
<223> OTHER INFORMATION: Synthetic construct

<400> SEQUENCE: 48

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80
```

-continued

```
Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Gln Leu
                165                 170                 175

Glu Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
            195                 200                 205

Lys Ser Leu Ser Leu Ser Leu Gly Gly Gly Gly Ser Gly Gly Gly
        210                 215                 220

Gly Ser Leu Glu Val Leu Phe Gln Gly Pro Gly Val Ser Ile Thr Lys
225                 230                 235                 240

Cys Ser Ser Asp Met Asn Gly Tyr Cys Leu His Gly Gln Cys Ile Tyr
                245                 250                 255

Leu Val Asp Met Ser Gln Asn Tyr Cys Arg Cys Glu Val Gly Tyr Thr
                260                 265                 270

Gly Val Ala Cys Glu His Phe Phe Leu Gly
            275                 280
```

<210> SEQ ID NO 49
<211> LENGTH: 282
<212> TYPE: PRT
<213> ORGANISM: Artificial Sequence
<220> FEATURE:
<223> OTHER INFORMATION: Synthetic construct

<400> SEQUENCE: 49

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160
```

```
Tyr Lys Thr Thr Pro Pro Val Leu Asp Ser Asp Gly Ser Phe Gln Leu
                165             170             175

Glu Ser Arg Leu Thr Val Asp Lys Ser Arg Trp Gln Glu Gly Asn Val
            180             185             190

Phe Ser Cys Ser Val Met His Glu Ala Leu His Asn His Tyr Thr Gln
        195             200             205

Lys Ser Leu Ser Leu Ser Leu Gly Gly Gly Gly Gly Ser Gly Gly Gly
    210             215             220

Gly Ser Leu Glu Val Leu Phe Gln Gly Pro Gly Val Ser Ile Thr Lys
225             230             235             240

Cys Ser Ser Asp Met Asn Gly Tyr Cys Leu His Gly Gln Cys Ile Tyr
            245             250             255

Leu Val Asp Met Ser Gln Asn Tyr Cys Arg Cys Glu Val Gly Tyr Thr
            260             265             270

Gly Val Arg Cys Glu His Ala Phe Leu Gly
            275             280
```

```
<210> SEQ ID NO 50
<211> LENGTH: 282
<212> TYPE: PRT
<213> ORGANISM: Artificial Sequence
<220> FEATURE:
<223> OTHER INFORMATION: Synthetic construct

<400> SEQUENCE: 50

Ala Pro Glu Ala Ala Gly Gly Pro Ser Val Phe Leu Phe Pro Pro Lys
1               5               10              15

Pro Lys Asp Thr Leu Met Ile Ser Arg Thr Pro Glu Val Thr Cys Val
            20              25              30

Val Val Asp Val Ser Gln Glu Asp Pro Glu Val Gln Phe Asn Trp Tyr
        35              40              45

Val Asp Gly Val Glu Val His Asn Ala Lys Thr Lys Pro Arg Glu Glu
    50              55              60

Gln Phe Asn Ser Thr Tyr Arg Val Val Ser Val Leu Thr Val Leu His
65              70              75              80

Gln Asp Trp Leu Asn Gly Lys Glu Tyr Lys Cys Lys Val Ser Asn Lys
            85              90              95

Gly Leu Pro Ser Ser Ile Glu Lys Thr Ile Ser Lys Ala Lys Gly Gln
            100             105             110

Pro Arg Glu Pro Gln Val Tyr Thr Leu Pro Pro Ser Gln Glu Glu Met
        115             120             125

Thr Lys Asn Gln Val Ser Leu Thr Cys Leu Val Lys Gly Phe Tyr Pro
    130             135             140

Ser Asp Ile Ala Val Glu Trp Glu Ser Asn Gly Gln Pro Glu Asn Asn
145             150             155             160

Tyr Lys Thr Thr Pro Pro Val Leu Asp Ser Asp Gly Ser Phe Gln Leu
                165             170             175

Glu Ser Arg Leu Thr Val Asp Lys Ser Arg Trp Gln Glu Gly Asn Val
            180             185             190

Phe Ser Cys Ser Val Met His Glu Ala Leu His Asn His Tyr Thr Gln
        195             200             205

Lys Ser Leu Ser Leu Ser Leu Gly Gly Gly Gly Gly Ser Gly Gly Gly
    210             215             220

Gly Ser Leu Glu Val Leu Phe Gln Gly Pro Gly Val Ser Ile Thr Lys
225             230             235             240
```

-continued

```
Cys Ser Ser Asp Met Asn Gly Tyr Cys Leu His Gly Gln Cys Ile Tyr
                245                 250                 255

Leu Val Asp Met Ser Gln Asn Tyr Cys Arg Cys Glu Val Gly Tyr Thr
                260                 265                 270

Gly Val Arg Cys Glu His Ala Lys Leu Gly
            275                 280

<210> SEQ ID NO 51
<211> LENGTH: 216
<212> TYPE: PRT
<213> ORGANISM: Artificial Sequence
<220> FEATURE:
<223> OTHER INFORMATION: Synthetic construct

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Ala Gly Lys Gly Leu Glu Trp Ile
            35                  40                  45

Gly Arg Ile Tyr Pro Ser Gly Asn Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Leu Val Met Asp Val Trp Gly Gln Gly Thr Leu Val Thr
                100                 105                 110

Val Ser Ser Ala Ser Thr Lys Gly Pro Ser Val Phe Pro Leu Ala Pro
                115                 120                 125

Cys Ser Arg Ser Thr Ser Glu Ser Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
            195                 200                 205

Val Asp Lys Arg Val Glu Ser Lys
        210                 215

<210> SEQ ID NO 52
<211> LENGTH: 213
<212> TYPE: PRT
<213> ORGANISM: Artificial Sequence
<220> FEATURE:
<223> OTHER INFORMATION: Synthetic construct

<400> SEQUENCE: 52

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Glu Phe Ser
                20                  25                  30

Tyr Leu Ala Trp Tyr Gln Gln Lys Pro Gly Gln Ala Pro Arg Leu Leu
```

-continued

```
          35                40                45

Ile Tyr Gly Ala Ser Ser Arg Ala Thr Gly Ile Pro Asp Arg Phe Ser
    50                55                60

Gly Ser Gly Ser Gly Thr Asp Phe Thr Leu Thr Ile Ser Arg Leu Glu
65                70                75                80

Pro Glu Asp Phe Ala Val Tyr Tyr Cys His Gln Tyr Gly Thr Asn Pro
                85                90                95

Phe Thr Phe Gly Gln Gly Thr Lys Val Glu Ile Lys Arg Thr Val Ala
                100               105               110

Ala Pro Ser Val Phe Ile Phe Pro Pro Ser Asp Glu Gln Leu Lys Ser
                115               120               125

Gly Thr Ala Ser Val Val Cys Leu Leu Asn Asn Phe Tyr Pro Arg Glu
    130               135               140

Ala Lys Val Gln Trp Lys Val Asp Asn Ala Leu Gln Ser Gly Asn Ser
145               150               155               160

Gln Glu Ser Val Thr Glu Gln Asp Ser Lys Asp Ser Thr Tyr Ser Leu
                165               170               175

Ser Ser Thr Leu Thr Leu Ser Lys Ala Asp Tyr Glu Lys His Lys Val
                180               185               190

Tyr Ala Cys Glu Val Thr Gln Gly Thr Thr Ser Val Thr Lys Ser Phe
    195               200               205

Asn Arg Gly Glu Cys
    210

<210> SEQ ID NO 53
<211> LENGTH: 439
<212> TYPE: PRT
<213> ORGANISM: Artificial Sequence
<220> FEATURE:
<223> OTHER INFORMATION: Synthetic construct

<400> SEQUENCE: 53

Gln Val Gln Leu Gln Glu Ser Gly Pro Gly Leu Val Lys Pro Ser Glu
1                 5                 10                15

Thr Leu Ser Leu Thr Cys Thr Val Ser Gly Gly Ser Ile Ser Ser Tyr
                20                25                30

Tyr Trp Ser Trp Ile Arg Gln Pro Ala Gly Lys Gly Leu Glu Trp Ile
        35                40                45

Gly Arg Ile Tyr Pro Ser Gly Asn Thr Asn Tyr Asn Pro Ser Leu Lys
    50                55                60

Ser Arg Val Thr Ile Ser Val Asp Thr Ser Lys Asn Gln Phe Ser Leu
65                70                75                80

Lys Leu Ser Ser Val Thr Ala Ala Asp Thr Ala Val Tyr Tyr Cys Ala
                85                90                95

Arg Gly Gly Leu Val Met Asp Val Trp Gly Gln Gly Thr Leu Val Thr
                100               105               110

Val Ser Ser Ala Ser Thr Lys Gly Pro Ser Val Phe Pro Leu Ala Pro
                115               120               125

Gly Ser Ala Ala Gln Thr Asn Ser Met Val Thr Leu Gly Cys Leu Val
    130               135               140

Lys Gly Tyr Phe Pro Glu Pro Val Thr Val Thr Trp Asn Ser Gly Ser
145               150               155               160

Leu Ser Ser Gly Val His Thr Phe Pro Ala Val Leu Gln Ser Asp Leu
                165               170               175

Tyr Thr Leu Ser Ser Ser Val Thr Val Pro Ser Ser Thr Trp Pro Ser
```

-continued

```
                 180               185               190
Glu Thr Val Thr Cys Asn Val Ala His Pro Ala Ser Ser Thr Lys Val
             195               200               205
Asp Lys Lys Ile Val Pro Arg Asp Cys Gly Cys Lys Pro Cys Ile Cys
         210               215               220
Thr Val Pro Glu Val Ser Ser Val Phe Ile Phe Pro Pro Lys Pro Lys
225               230               235               240
Asp Val Leu Thr Ile Thr Leu Thr Pro Lys Val Thr Cys Val Val Val
             245               250               255
Asp Ile Ser Lys Asp Asp Pro Glu Val Gln Phe Ser Trp Phe Val Asp
         260               265               270
Asp Val Glu Val His Thr Ala Gln Thr Gln Pro Arg Glu Glu Gln Phe
     275               280               285
Asn Ser Thr Phe Arg Ser Val Ser Glu Leu Pro Ile Met His Gln Asp
     290               295               300
Trp Leu Asn Gly Lys Glu Phe Lys Cys Arg Val Asn Ser Ala Ala Phe
305               310               315               320
Pro Ala Pro Ile Glu Lys Thr Ile Ser Lys Thr Lys Gly Arg Pro Lys
             325               330               335
Ala Pro Gln Val Tyr Thr Ile Pro Pro Pro Lys Glu Gln Met Ala Lys
             340               345               350
Asp Lys Val Ser Leu Thr Cys Met Ile Thr Asp Phe Phe Pro Glu Asp
             355               360               365
Ile Thr Val Glu Trp Gln Trp Asn Gly Gln Pro Ala Glu Asn Tyr Lys
     370               375               380
Asn Thr Gln Pro Ile Met Asp Thr Asp Gly Ser Tyr Phe Val Tyr Ser
385               390               395               400
Lys Leu Asn Val Gln Lys Ser Asn Trp Glu Ala Gly Asn Thr Phe Thr
             405               410               415
Cys Ser Val Leu His Glu Gly Leu His Asn His His Thr Glu Lys Ser
         420               425               430
Leu Ser His Ser Pro Gly Lys
         435
```

```
<210> SEQ ID NO 54
<211> LENGTH: 215
<212> TYPE: PRT
<213> ORGANISM: Artificial Sequence
<220> FEATURE:
<223> OTHER INFORMATION: Synthetic construct

<400> SEQUENCE: 54

Glu Ile Val Leu Thr Gln Ser Pro Gly Thr Leu Ser Leu Ser Pro Gly
1               5                10                15
Glu Arg Ala Thr Leu Ser Cys Arg Ala Ser Gln Ser Val Glu Phe Ser
             20                25                30
Tyr Leu Ala Trp Tyr Gln Gln Lys Pro Gly Gln Ala Pro Arg Leu Leu
         35                40                45
Ile Tyr Gly Ala Ser Ser Arg Ala Thr Gly Ile Pro Asp Arg Phe Ser
     50                55                60
Gly Ser Gly Ser Gly Thr Asp Phe Thr Leu Thr Ile Ser Arg Leu Glu
65                70                75                80
Pro Glu Asp Phe Ala Val Tyr Tyr Cys His Gln Tyr Gly Thr Asn Pro
             85                90                95
Phe Thr Phe Gly Gln Gly Thr Lys Val Glu Ile Lys Arg Thr Val Ala
```

-continued

```
                100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215
```

<210> SEQ ID NO 55
<211> LENGTH: 47
<212> TYPE: PRT
<213> ORGANISM: Homo sapiens

<400> SEQUENCE: 55

```
Lys Phe Ser His Leu Cys Leu Glu Asp His Asn Ser Tyr Cys Ile Asn
1                   5                   10                  15

Gly Ala Cys Ala Phe His His Glu Leu Glu Lys Ala Ile Cys Arg Cys
                20                  25                  30

Phe Thr Gly Tyr Thr Gly Glu Arg Cys Glu His Leu Thr Leu Thr
            35                  40                  45
```

<210> SEQ ID NO 56
<211> LENGTH: 47
<212> TYPE: PRT
<213> ORGANISM: Homo sapiens

<400> SEQUENCE: 56

```
Lys Lys Lys Asn Pro Cys Asn Ala Glu Phe Gln Asn Phe Cys Ile His
1                   5                   10                  15

Gly Glu Cys Lys Tyr Ile Glu His Leu Glu Ala Val Thr Cys Lys Cys
                20                  25                  30

Gln Gln Glu Tyr Phe Gly Glu Arg Cys Gly Glu Lys Ser Met Lys
            35                  40                  45
```

<210> SEQ ID NO 57
<211> LENGTH: 46
<212> TYPE: PRT
<213> ORGANISM: Homo sapiens

<400> SEQUENCE: 57

```
Lys Lys Arg Asp Pro Cys Leu Arg Lys Tyr Lys Asp Phe Cys Ile His
1                   5                   10                  15

Gly Glu Cys Lys Tyr Val Lys Glu Leu Arg Ala Pro Ser Cys Ile Cys
                20                  25                  30

His Pro Gly Tyr His Gly Glu Arg Cys His Gly Leu Ser Leu
            35                  40                  45
```

<210> SEQ ID NO 58
<211> LENGTH: 48
<212> TYPE: PRT
<213> ORGANISM: Homo sapiens -continued

```
<400> SEQUENCE: 58

Gly His Phe Ser Arg Cys Pro Lys Gln Tyr Lys His Tyr Cys Ile Lys
1               5                   10                  15

Gly Arg Cys Arg Phe Val Val Ala Glu Gln Thr Pro Ser Cys Val Cys
            20                  25                  30

Asp Glu Gly Tyr Ile Gly Ala Arg Cys Glu Arg Val Asp Leu Phe Tyr
        35                  40                  45

<210> SEQ ID NO 59
<211> LENGTH: 50
<212> TYPE: PRT
<213> ORGANISM: Homo sapiens

<400> SEQUENCE: 59

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
            20                  25                  30

Val Cys His Ser Gly Tyr Val Gly Ala Arg Cys Glu His Ala Asp Leu
        35                  40                  45

Leu Ala
    50

<210> SEQ ID NO 60
<211> LENGTH: 49
<212> TYPE: PRT
<213> ORGANISM: Homo sapiens

<400> SEQUENCE: 60

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp
```